(12) United States Patent
Leblond et al.

(10) Patent No.: US 7,923,579 B2
(45) Date of Patent: Apr. 12, 2011

(54) TRICYCLIC HYDROXAMATE AND BENZAMIDE DERIVATIVES, COMPOSITIONS AND METHODS

(75) Inventors: Bertrand Leblond, Rouen (FR); Eric Beausoleil, Paris (FR)

(73) Assignee: Exonhit Therapeutics S.A., Paris (FR)

( * ) Notice: Subject to any disclaimer, the term of this patent is extended or adjusted under 35 U.S.C. 154(b) by 1341 days.

(21) Appl. No.: 10/581,947

(22) PCT Filed: Dec. 10, 2004

(86) PCT No.: PCT/IB2004/004334
§ 371 (c)(1),
(2), (4) Date: Jun. 6, 2006

(87) PCT Pub. No.: WO2005/058803
PCT Pub. Date: Jun. 30, 2005

(65) Prior Publication Data
US 2007/0129368 A1    Jun. 7, 2007

(30) Foreign Application Priority Data

Dec. 12, 2003   (EP) .................... 03293143

(51) Int. Cl.
| C07C 221/00 | (2006.01) |
| C07C 223/00 | (2006.01) |
| C07C 225/00 | (2006.01) |
| A01N 33/00  | (2006.01) |
| A61K 31/13  | (2006.01) |
| A61K 31/16  | (2006.01) |

(52) U.S. Cl. ...................... 564/342; 514/579
(58) Field of Classification Search .......... None
See application file for complete search history.

(56) References Cited

U.S. PATENT DOCUMENTS 4,829,080 A * 5/1989 Maignan et al. ............. 514/432
5,567,721 A * 10/1996 Bernardon et al. .......... 514/353

FOREIGN PATENT DOCUMENTS

| EP | 0 382 076 A1 | 8/1990 |
| WO | 97/33856 A   | 9/1997 |
| WO | 01/38322 A   | 5/2001 |
| WO | 01/56358   * | 8/2001 |
| WO | 02/22577 A   | 3/2002 |
| WO | 02/098363 A  | 12/2002 |

OTHER PUBLICATIONS

Morissette et al. Advanced Drug Delivery Reviews 2004, 56, 275-300.*
Vippagunta et al. Advanced Drug Delivery Reviews 2001, 48, 3-26, abstract.*
International Search Report of PCT/IB2004/004334, mailed Apr. 22, 2005.
Zacheis et al., "Heteroarotinoids Inhibit Head and Neck Cancer Cell Lines in Vitro and in Vivo Through Both RAR and RXR Retinoic Acid Receptors", Journal of Medicinal Chemistry, 1999, vol. 42, No. 21, pp. 4434-4445, XP002278654.
Lavoie et al., "Design and Synthesis of a Novel Class of Histone Deacetylase Inhibitors", Bioorganic & Medicinal Chemistry Letters, vol. 11, No. 21, 2001, pp. 2847-2850, XP002954135.

* cited by examiner

*Primary Examiner* — Daniel M Sullivan
*Assistant Examiner* — Clinton Brooks
(74) *Attorney, Agent, or Firm* — Nixon & Vanderhye P.C.

(57) ABSTRACT

The present invention relates to compounds and methods for inhibiting histone deacetylase enzymatic activity. The present invention also pertains to pharmaceutical compositions comprising such compounds, and the use of such compounds and compositions, both in vitro and in vivo, to inhibit histone deacetylases (IIDACs), and in the treatment of conditions mediated by HDAC, cancer, proliferative conditions, psoriasis, and also central nervous system diseases. It further deals with processes for preparing said compounds.

7 Claims, 11 Drawing Sheets

Figure 1:
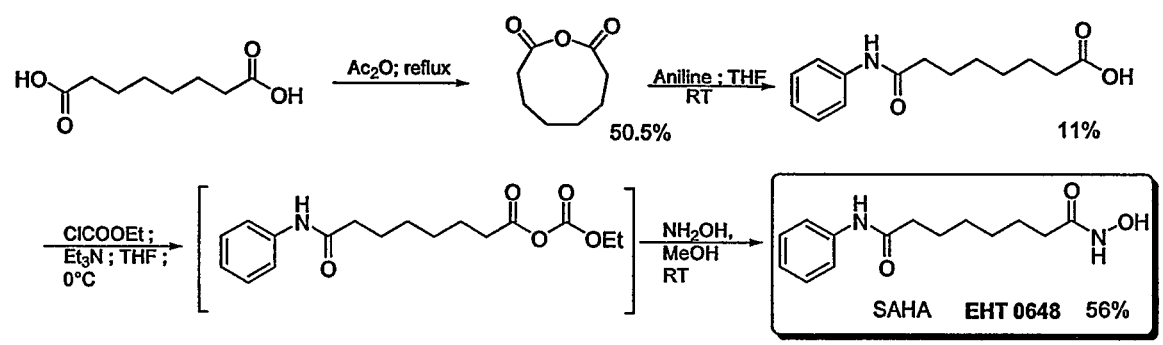

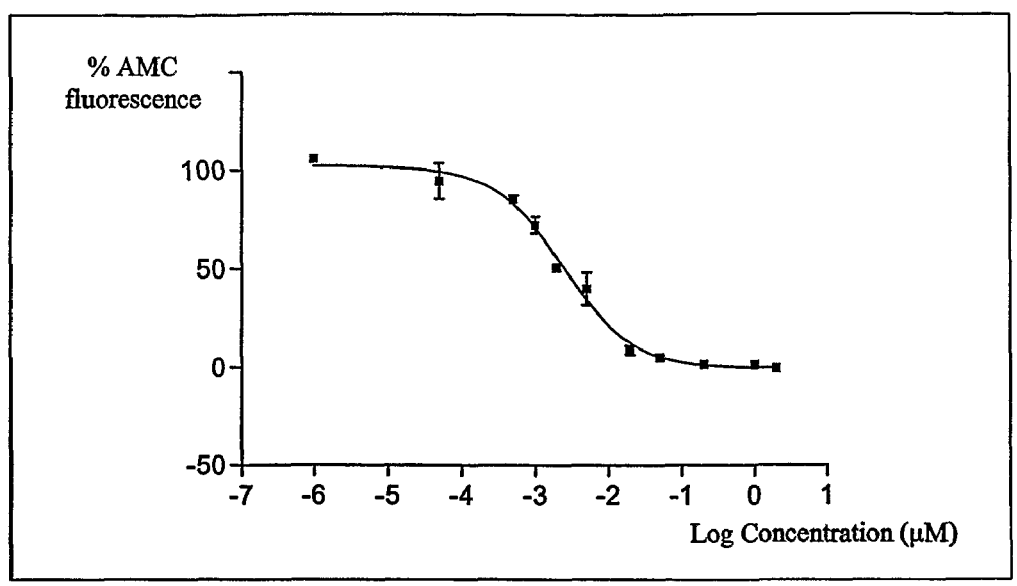
Figure 10A
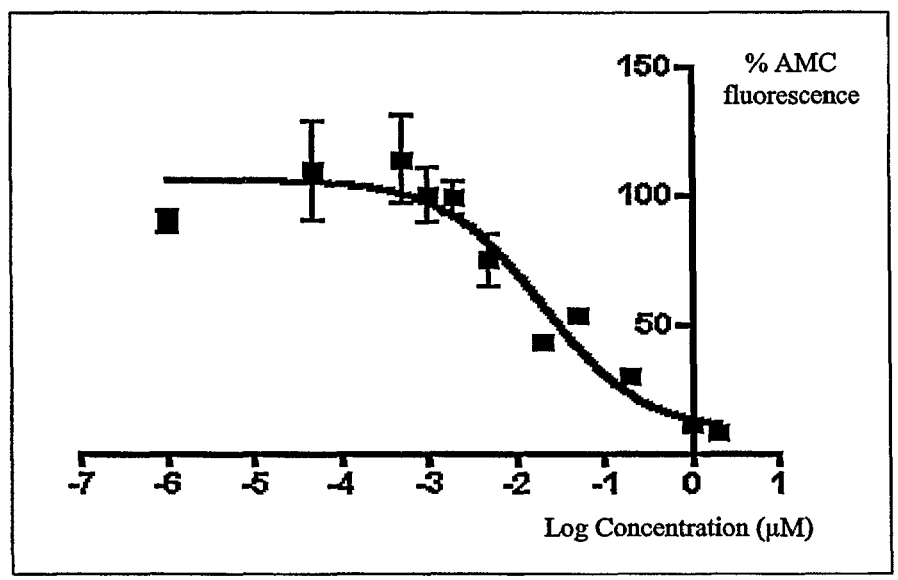
Figure 10 B
FIGURE 10

TRICYCLIC HYDROXAMATE AND BENZAMIDE DERIVATIVES, COMPOSITIONS AND METHODS

This application is the US national phase of international application PCT/IB2004/004334, filed 10 Dec. 2004, which designated the U.S. and claims priority of EP 03293143.8, filed 12 Dec. 2003, the entire contents of each of which are hereby incorporated by reference.

FIELD OF THE INVENTION

The invention relates to compounds and their uses, particularly in the pharmaceutical industry. More particularly, the invention relates to compounds and methods for inhibiting histone deacetylase enzymatic activity. The present invention also pertains to pharmaceutical compositions comprising such compounds, and the use of such compounds and compositions, both in vitro and in vivo, to inhibit histone deacetylases (HDACs), and in the treatment of conditions mediated by HDAC, cancer, proliferative conditions, psoriasis, and also central and peripheral nervous system diseases. It further deals with processes for preparing said compounds.

BACKGROUND OF THE INVENTION

Compounds which inhibit HDACs catalyze the removing of the acetyl group from lysine residues in the N-terminal tails of nucleosomal core histones resulting in a more compact chromatin structure, a configuration that is generally associated with repression of transcription (Davie J. R. et al., J. Cell. Biochem. suppl. 30-31, 203-213, 1998). HDACs are involved in cell-cycle progression and differentiation, and their deregulation is associated with several cancers. HDAC inhibitors, such as trichostatin A (TSA) and suberoylanilide hydroxamic acid (SAHA), have anti-tumour effects, as they can inhibit cell growth, induce terminal differentiation and prevent the formation of tumours in mice models, and they are effective in the treatment of promyelocytic leukaemia (Finnin M. S. et al., Nature, 401, 188-193, 1999 and references therein). Trichostatin A has also been reported to be useful in the treatment of fibrosis, e.g. liver fibrosis and liver chirrhosis. (European Patent Application EP 0 827 742, published 11 Mar., 1998). Recent evidences have been found than certain HDAC inhibitor (e.g. SAHA) can cross the blood brain barrier to inhibit HDAC activity causing the accumulation of acetylated histones in the brain (WO 03032921). SAHA has been shown to dramatically improve the motor impairment in R6/2 mice, clearly validating the pursuit of this class of compounds as Huntington's disease (HD) therapeutics. More generally HDAC inhibitors could be useful for treating diseases of the central nervous system (CNS) in particular neurodegenerative diseases inherited such as polyglutamine expansion diseases (e.g. HD, Steffan J. et al., Nature, 413, 739-744, 2001 and Hockly E. et al., PNAS 100(4), 2041-2046, 2003).

Nine human HDAC have been characterized and two inferred; these members fall into two related classes (Class I and Class II). HDAC 1, 2, 3 and 8 belong to the human Class I that has homology to the yeast protein rpd3. They are located in the nucleus, and are found in complexes associated with transcriptional corepressors. The class II enzyme has six representatives so far (HDAC 4-6 and 7-10) and they all show homology to the related yeast enzyme HDA1 and are found in both the nucleus and cytoplasm. Both class I and II HDACs are inhibited by SAHA and related hydroxamic acid-based HDAC inhibitors. Class III HDACs form a structurally distant class of NAD-dependent enzymes that are related to the yeast SIR2 proteins and are not inhibited by hydroxamic acid-based HDAC inhibitors (Proc. Natl. Acad. Sci. USA, Vol. 99, Issue 18, 11700-11705, Sep. 3, 2002)

A very few of small molecules are known that selectively target either the two classes (class I or II) or individual members (HDAC1-10) of this family (Stenson S. et al., Org. Lett., 26(3), 4239-4242, 2001).

Some of the compounds of the present invention have also been designed to be able to cross the blood brain barrier as they have low molecular weight and a calculated polar surface area (PSA)<90 $Å^2$.

There is still a need for high enzymatic activity and more selective HDAC inhibitors with little or no side effects.

The novel compounds of the present invention solve the above-described problem. The compounds differ from the prior art in structure. The compounds of the present invention show good in vitro histone deacetylase inhibiting enzymatic activity.

Accordingly, one aspect of the invention is to provide a compound having a general formula (I):

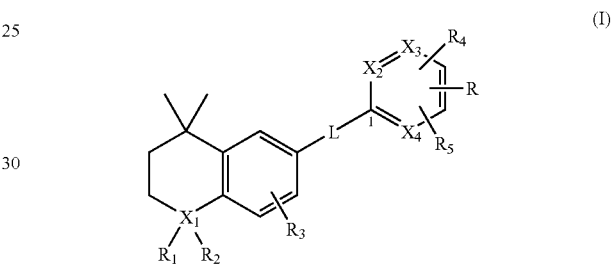

(I)

wherein:
R is —C(O)NR$_7$R$_8$, —(CXY)$_t$C(O)NR$_7$R$_8$, —C(O)C(O)NHMe, —(C=C)C(O) NR$_8$R$_9$, —C(O)CF$_3$, or another Zn-chelating-group, with the proviso that R is not an acidic group or an ester derivative, —COOR$_9$ or salt thereof, R$_7$ is a group of formula —OH, —OR$_9$, 2-aminophenyl and R$_8$ is selected from hydrogen, C$_{1-6}$alkyl; R$_9$ is independently selected from hydrogen or C$_{1-6}$alkyl; t is 1, 2 or 3 (preferably 1), X and Y, which are identical or different, represent an hydrogen or halogen atom (preferably F), X$_1$ represents a carbon, oxygen, nitrogen or sulphur atom, R$_1$ and R$_2$ represent independently or form together:
  a C$_{1-6}$alkyl group, in particular methyl or ethyl groups, when X$_1$ is an atom of carbon,
  nothing, when X$_1$ is an atom of oxygen or an atom of sulphur,
  one or two atoms of oxygen, when X$_1$ is an atom of sulphur (the case of a sulfoxide —SO— or a sulphone —SO$_2$—), or
  one atom of hydrogen, an alkyl, aryl or aralkyl group, when X$_1$ is an atom of nitrogen (the case of an amino —NH, -an N-alkyl, N-aryl or N-aralkyl group);

X$_2$ and X$_3$, which are identical or different, represent CH, an atom of oxygen or an atom of nitrogen, or X$_2$=X$_3$ may be a single atom of sulphur, oxygen or nitrogen, or in the case where X$_2$ is an atom of oxygen and X$_3$ an atom of nitrogen, C$_1$ and X$_4$ represent a single one and same carbon atom, so that the ring carrying X$_2$ and X$_3$ can be an isoxazole ring, X$_4$ can be CH or a nitrogen atom, R$_4$ and R$_5$, which are identical or different, represent a hydrogen atom, a halogen atom, more particularly a fluorine atom, a C$_{1-6}$alkyl group, a group of formula —OH, —NH$_2$, —NHR$_6$, —OR$_6$, —SR$_6$, —(CF$_2$)$_n$CF$_3$, where n is an integer from 0 to 10, and whenever possible their salts with physiologically tolerated acids, R$_6$ represents a hydrogen atom, a C$_{1-6}$alkyl group, a fluoroalkyl group having from 1 to 6 carbons atoms and from 3 to 7 fluorine atoms, an aryl group or an aralkyl group;

R$_3$ has the same definition as R$_4$ and R$_5$;

L is a linker and represents a bivalent radical either linear or cyclic, either saturated or unsaturated, more particularly L represents a bivalent radical derived from an alkane, alkene, alkyne or, aromatic or not, cyclic containing hydrocarbon group having from 1 to 12 carbon atoms, another bivalent radical of the following formula —O—, —CO—, —CO—NH—, —NH—CO—, —NH—CO—NH—, —CF$_2$—CO—NH—, —C(XY)—CO—NH—CH$_2$—, —NH—CO—CO—NH—, —NH—CO—CO—NH—CH$_2$—, —SO$_2$NH—, —NHSO$_2$—, —SO$_2$NCH$_3$—, —NCH$_3$SO$_2$—, —NR$_6$—, —C(=NOH)—, or a mixture thereof; R$_6$ being as defined above, optionally the bivalent radical is substituted, in particular by at least one C$_{1-6}$alkyl group; X and Y, which are identical or different, represent an hydrogen or halogen atom (preferably F);

its tautomers, optical and geometrical isomers, racemates, salts, hydrates and mixtures thereof.

The compounds of the present invention may have one or more asymmetric centers and it is intended that stereoisomers (optical isomers), as separated, pure or partially purified stereoisomers or racemic mixtures thereof are included in the scope of the invention.

The present invention more particularly deals with the compounds of the present invention for use as a medicine.

The present invention also relates to pharmaceutical compositions comprising at least one compound as defined above in a pharmaceutically acceptable support, optionally in association with another active agent.

The pharmaceutical composition is more particularly intended to treat conditions mediated by HDAC, such as cancers, in particular promyelocytic leukaemia, other diseases associated with abnormal cell proliferation, such as psoriasis, and also central and peripheral nervous system diseases and neurodegenerative diseases associated with an excitotoxicity, such as Huntington's disease, such as polyglutamine expansion diseases, Alzheimer disease, Parkinson disease, multiple sclerosis, neuronal ischemia and amyotrophic lateral sclerosis (ALS). The pharmaceutical composition is also more particularly useful in the treatment of fibrosis, e.g. liver fibrosis and liver chirrhosis.

The present invention also relates to the use of a compound as defined above, for the manufacture of a medicament for the treatment of conditions mediated by HDAC, such as cancers, in particular promyelocytic leukaemia, other diseases associated with abnormal cell proliferation, such as psoriasis, and also central and peripheral nervous system diseases and neurodegenerative diseases associated with an excitotoxicity, such as Huntington's disease, such as polyglutamine expansion diseases, Alzheimer disease, Parkinson disease, multiple sclerosis, neuronal ischemia and amyotrophic lateral sclerosis (ALS). It also deals with the use of a compound as defined above, for the manufacture of a medicament for the treatment of fibrosis, e.g. liver fibrosis and liver chirrhosis.

The present invention also includes methods of conditions mediated by HDAC, such as cancers, other diseases associated with abnormal cell proliferation, such as psoriasis, and also central and peripheral nervous system diseases and neurodegenerative diseases associated with an excitotoxicity as identified above, comprising the administration to a subject in need thereof of an effective amount of a compound as defined above.

As will be further disclosed in this application, the compounds according to this invention have strong HDAC inhibitory activity and are effective at reducing or arresting growth of proliferating cells such as tumour cells.

PREFERRED EMBODIMENTS

Within the context of the present application, the term alkyl denotes linear or branched saturated groups containing from 1 to 10 carbon atoms, preferably from 1 to 6 carbon atoms. Examples of alkyl groups having from 1 to 10 carbon atoms inclusive are methyl, ethyl, n-propyl, isopropyl, t-butyl, n-butyl, pentyl, hexyl, heptyl, octyl, nonyl, decyl, 1-methylethyl, 2-methylpropyl, 2-ethylhexyl, 2-methylbutyl, 2-methylpentyl, 1-methylhexyl, 3-methylheptyl and the other isomeric forms thereof.

The term alkenyl denotes for hydrocarbon groups that have at least one double bond between carbon atoms. The alkenyl groups may be linear or branched. Examples of alkenyl containing from 2 to 6 carbon atoms are 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl and the isomeric forms thereof (both geometric isomers, cis and/or trans forms).

The term alkynyl denotes for hydrocarbon groups that have at least one triple bond between carbon atoms. The alkynyl groups may be linear or branched. Examples of alkynyl containing from 2 to 6 carbon atoms are 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl. The simplest alkyne is ethyne (acetylene).

The term aryl includes any aromatic group comprising preferably from 5 to 14 carbon atoms, preferably from 6 to 14 carbon atoms, optionally interrupted by one or several heteroatoms selected from N, O, S or P. Most preferred aryl groups are mono- or bi-cyclic and comprises from 6 to 14 carbon atoms, such as phenyl, α-naphtyl, β-naphtyl, antracenyl, or fluorenyl group. The heteroaryl groups include, but are not limited to, pyrrolyl, furyl, thienyl, pyridyl, pyrimidyl, or quinolyl.

The term aralkyl group generally stands for an aryl group attached to an alkyl group as defined above, such as benzyl or phenethyl.

The bivalent radical is a radical derived by removal of two hydrogen atoms from the mononuclear parent hydrides, such as an alkane, alkene, or alkyne; the bivalent radicals can also be named as alkanediyl, alkenediyl, or alkynediyl. The bivalent radical may also correspond to an aromatic or not, cyclic containing hydrocarbon group having from 1 to 12 carbon atoms. The aromatic or not, cyclic containing hydrocarbon group includes aryl groups as defined above (in particular phenyl, pyridyl, indolyl, benzofuryl or pyrrolyl) and cycloalkyl or -alkenyl groups, (in particular cyclopropyl or cyclohexyl groups). The aromatic or not, cyclic containing hydrocarbon group can optionally be interrupted by one or several heteroatoms selected from N, O, S or P (also named heterocyclic ring). The bivalent radical L can also be a mixture of at least two bivalent radicals as defined above.

According to a particular embodiment, the groups identified above can be substituted with at least one substituent, which may be selected from the group consisting in: a hydrogen atom, a halogen atom (preferably F, Cl, or Br), a hydroxyl group, a C$_{1-10}$alkyl group, an alkenyl group, an C$_{1-10}$alkanoyl group, a (C$_1$-C$_{10}$)alkoxy group, a (C$_1$-C$_{10}$)alkoxycarbonyl group, an aryl group, an aralkyl group, an arylcarbonyl group, a mono- or poly-cyclic hydrocarbon group, a —NHCO($C_1$-$C_6$)alkyl group, —$NO_2$, —CN, a —Nrr' group or a trifluoro ($C_1$-$C_6$)alkyl group, r and r', which are identical or different, represent a hydrogen atom, a lower alkyl group, an aryl or aralkyl group, an α-aminoacid group, a sugar group or a heterocyclic group, or in which r and r' taken together form a heterocyclic ring.

An alkanoyl group is a —CO-alkyl group, the alkyl group being as defined above.

The term arylcarbonyl group generally stands for an aryl group attached to a carbonyl group, the aryl group being as defined above.

The term alkoxycarbonyl group generally stands for an alkoxy group attached to a carbonyl group, the alkoxy group being a —O-alkyl group (alkyl is as defined above).

The term mono- or poly-cyclic hydrocarbon group is understood to refer to hydrocarbon cyclic group having from 1 to 20 carbon atoms, optionally interrupted with one or more heteroatoms selected in the group N, O, S and P. Among such mono- or poly-cyclic hydrocarbon groups, cyclopentyl, cyclohexyl, cycloheptyl, 1- or 2-adamantyl groups, pyran, piperidine, pyrrolidine, morpholine, dioxan, tetrahydrothiophene, and tetrahydrofuran can be cited. The mono- or poly-cyclic hydrocarbon group may form with the phenyl group it is attached an aryl group, such as a α-naphtyl, β-naphtyl, or antracenyl group.

As used in the foregoing definitions and hereinafter, halo is generic to fluoro, chloro, bromo and iodo. The trifluoro($C_1$-$C_6$)alkyl group is preferably the trifluoromethyl group.

The term "histone deacetylase inhibitor" or "inhibitor of histone deacetylase" is used to identify a compound, which is capable of interacting with a histone deacetylase and inhibiting its activity, more particularly its enzymatic activity. Unless otherwise indicated by context, the term "histone" is meant to refer to any histone protein, including HI, H2A, H2B, H3, H4, and H5, from any species. Human HDAC proteins or gene products, include, but are not limited to, HDAC-1, HDAC-2, HDAC-3, HDAC-4, HDAC-5, HDAC-6, HDAC-7, HDAC-8, HDAC-9 and HDAC-10. The histone deacetylase can also be derived from a protozoal or fungal source. Inhibiting histone deacetylase enzymatic activity means reducing the ability of a histone deacetylase to remove an acetyl group from a histone. Preferably, such inhibition is specific, i.e. the histone deacetylase inhibitor reduces the ability of a histone deacetylase to remove an acetyl group from a histone at a concentration that is lower than the concentration of the inhibitor that is required to produce some other, unrelated biological effect.

The term "another Zn-chelating group" refers to a group, which is capable of interacting with a Zn-ion, which can be present at an enzymatic binding site.

According to preferred embodiments, the compounds according to the invention correspond to general formula (I) wherein R is in para position or meta position of C1, R is preferably in para position of C1.

According to preferred embodiments, the compounds according to the invention correspond to general formula (I) wherein R is —C(O)$NR_7R_8$ or —(CXY)$_t$C(O)$NR_7R_8$, in particular wherein $R_8$ is an hydrogen atom and $R_7$ is an hydroxyl group or a 2-aminophenyl group, preferably with X and Y are both halogen atoms and t is 1. More preferably, R is an hydroxamic acid group (—(C=O)—NH—OH), a 2,2-difluoro-N-hydroxyacetamido group (—$CF_2$—(C=O)—NH—OH), a N-(2-aminophenyl)acetamido group.

In another embodiment, R is another zinc chelator group, in particular electrophilic ketones, such as —(C=O)—$CF_3$ or α-ketoamides, for instance —(C=O)—(C=O)—NHMe.

According to preferred embodiments, the compounds according to the invention correspond to general formula (I) wherein L represents —CO—NH—, —NH—CO—, —CH=CH— (cis or trans forms), —$CF_2$—CO—NH—, —$CF_2$—CO—NH—$CH_2$—, or —NH—CO—CO—NH—.

According to preferred embodiments, the compounds of the invention correspond to general formula (I) wherein $R_3$ is an hydrogen atom, $OR_6$, in particular methoxy, or a $C_{1-6}$alkyl group, in particular methyl. $R_3$ is advantageously on position 2 of the substituted naphthalene derivative.

According to preferred embodiments, the compounds according to the invention correspond to general formula (I) wherein the ring carrying $X_1$ is selected from:

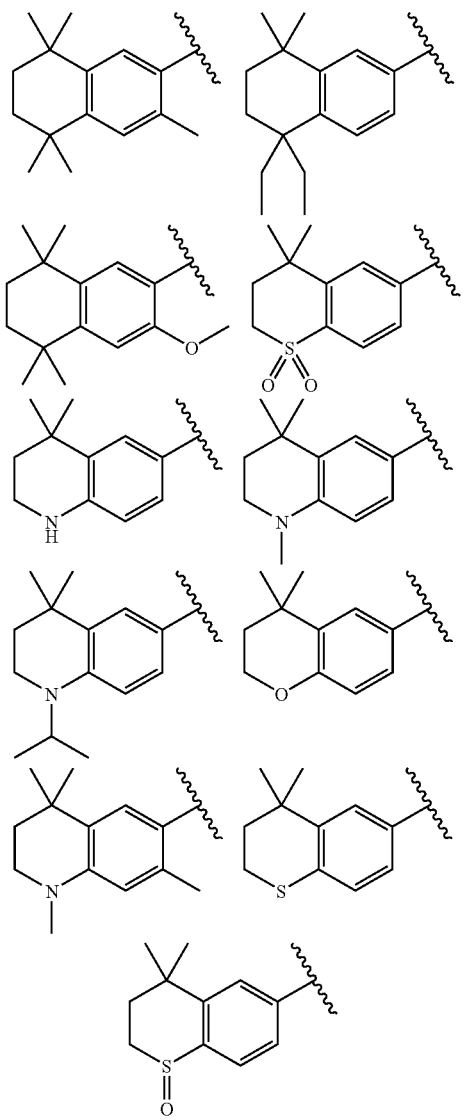

Chemical variations around this lipophilic head called 1,1,4,4-tetramethyltetrahydronaphtalene have been developed in the last twenty years for synthetic retinoids (also called retinobenzoic acids, arotinoids heteroarotinoids, or more recently rexinoids) and are well described and known by the man of the art: The Retinoids-Biology, Chemistry and Medicine; Sporn M. B. et al.; Eds.; Raven Press: New York, 1994 and The Retinoids; Sporn, M. B. et al.; Eds.; Academic Press: Orlando, 1984. See also Waugh, K. M. et al., J. Med. Chem. 27, 116-124, 1985; Spruce L. W. et al., J. Med. Chem., 34, 430-439, 1991; Spruce L. W. et al., J. Med. Chem., 30, 1474-1482, 1987;. Benbrook et al., J. Med. Chem., 40, 3567-3583, 1997; Benbrook et al., J. Med. Chem., 41, 3753-3757, 1998; Dhar, A. et al., J. Med. Chem., 42, 3602-3614, 1999; Zacheis D. Et al., J. Med. Chem., 42, 4434-4445, 1999; Leblond B. et al. U.S. Pat. No. 6,265,423 and references therein.

According to preferred embodiments, the compounds according to the invention correspond to general formula (I) wherein the ring carrying $X_2$, $X_3$ and $X_4$ is selected from phenyl, pyridinyl, pyrimidinyl, isoxazolyl, thiophenyl, furanyl, pyrollyl, pyrazolyl, imidazolyl, isothiazolyl, thiazolyl, thienyl, thienooxazolyl and triazinyl rings. More preferably, said ring is phenyl, optionally substituted by a halogen atom, more particularly a fluorine atom, a $C_{1-6}$alkyl group, a group of formula —OH, or $OR_6$.

Said chemical variations around this second ring moiety are also well known by the man in the art. One of ordinary skill in the art can readily substitute isosteres and bioisosteres of phenyl ring to a phenyl ring. Such isosteres or bioisoteres are, for instance, pyridinyl, pyrimidinyl, isoxazolyl, thiophenyl, furanyl, pyrollyl, pyrazolyl, imidazolyl, isothiazolyl, thiazolyl, thienyl, thienooxazolyl and triazinyl rings.

When the compounds according to the invention are in the forms of salts, they are preferably pharmaceutically acceptable salts. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

The pharmaceutically acceptable salts are prepared by reacting the compound of formula I with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol, etc. Mixture of solvents may be used. Organic bases like lysine, arginine, diethanolamine, choline, guanidine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, fonic acid, acetic acid, citric acid, maleic acid, salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane, etc. Mixture of solvents may also be used.

Specific examples of compounds of formula (I) which fall within the scope of the present invention include the following compounds:
N-(4-(Hydroxycarbamoyl)phenyl)-5,6,7,8-tetrahydro-5,5,8, 8-tetramethylnaphthalene-2-carboxamide EHT 3741
N-(4-(2-Aminophenylcarbamoyl)phenyl)-5,6,7,8-tetrahydro-5,5,8,8-tetramethyl-naphthalene-2-carboxamide EHT 1800
N-(1,2,3,4-Tetrahydro-1,1,4,4-tetramethylnaphthalen-6-yl)-N'-hydroxyterephthalamide EHT 7706
4-((E)-2-(1,2,3,4-tetrahydro-1,1,4,4-tetramethylnaphthalen-6-yl)vinyl)-N-hydroxybenzamide EHT 9899
4-((Z)-2-(1,2,3,4-tetrahydro-1,1,4,4-tetramethylnaphthalen-6-yl)vinyl)-N-hydroxybenzamide EHT 7786
4-(2,2-difluoro-2-(1,2,3,4-tetrahydro-1,1,4,4-tetramethyl-naphthalen-7-yl)acetamido)-N-hydroxybenzamide EHT 9299
3-(2,2-difluoro-2-(1,2,3,4-tetrahydro-1,1,4,4-tetramethyl-naphthalen-7-yl)acetamido)-N-hydroxybenzamide EHT 9710
4-((2,2-difluoro-2-(1,2,3,4-tetrahydro-1,1,4,4-tetramethyl-naphthalen-7-yl)acetamido)methyl)-N-hydroxybenzamide EHT 7800
N-(4-((hydroxycarbamoyl)difluoromethyl)phenyl)-5,6,7,8-tetrahydro-5,5,8,8-tetramethylnaphthalene-2-carboxamide EHT 4996
N-(4-Hydroxycarbamoyl-phenyl)-N'-(5,5,8,8-tetramethyl-5, 6,7,8-tetrahydro-naphthalen-2-yl)-oxalamide EHT 0933
N-(4-hydroxycarbamoyl-benzyl)-N'-(5,5,8,8-tetramethyl-5, 6,7,8-tetrahydro-naphthalen-2-yl)-oxalamide EHT 6028

The preferred compounds of the invention are:
4-(2,2-Difluoro-2-(1,2,3,4-tetrahydro-1,1,4,4-tetramethyl-naphthalen-7-yl)acetamido)-N-hydroxybenzamide EHT 9299
N-(1,2,3,4-Tetrahydro-1,1,4,4-tetramethylnaphthalen-6-yl)-N'-hydroxyterephthalamide EHT 7706
4-((2,2-Difluoro-2-(1,2,3,4-tetrahydro-1,1,4,4-tetramethyl-naphthalen-7-yl)acetamido)methyl)-N-hydroxybenzamide EHT 7800
N-(4-(Hydroxycarbamoyl)phenyl)-5,6,7,8-tetrahydro-5,5,8, 8-tetramethylnaphthalene-2-carboxamide EHT 3741

The compounds according to the present invention may be prepared by various methods known to those skilled in the art. More specifically, the following chemical routes have been carried out.

The reference compound SAHA or EHT 0648 (FIG. 1) was prepared in three steps following the route described by A. Mai et al., OPPI Briefs, vol. 33, No 4, 391-394, 2001.

Figure 2:
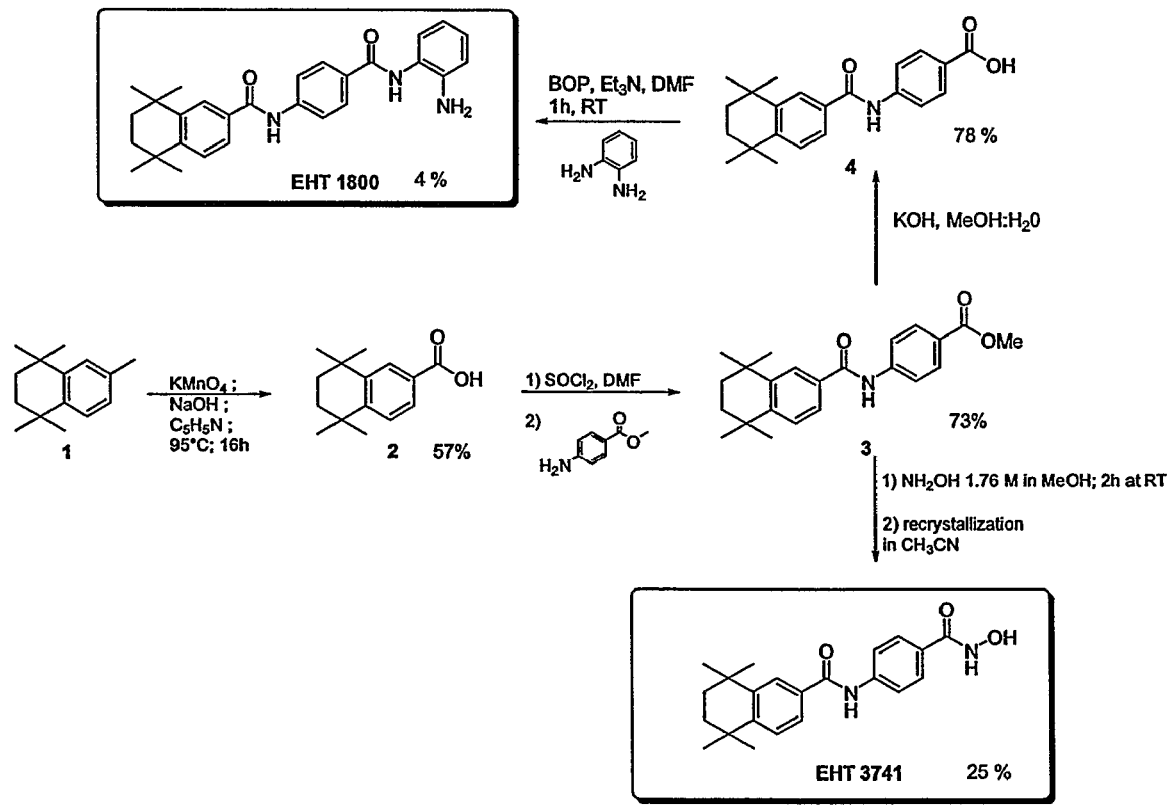

EHT 3741 and EHT 1800 were prepared in three steps from commercial 1,1,4,4,6-pentamethyltetrahydronaphtalene 1 (FIG. 2). Oxidation with potassium permanganate in presence of NaOH in pyridine at 95° C. for 16 h afforded to the corresponding acid 2 in 57% yield. The acid 2 was coupled to methyl 4-aminobenzoate in dichloromethane, using triethylamine as base, via its acid chloride formation in $SOCl_2$ in presence of a catalytic amount of DMF. Finally, the obtained methyl ester derivative 3 was reacted for 2 hours at room temperature with a solution of NH₂OH 1.76 M in MeOH to afford to EHT 3741 in pure form after recrystallization in acetonitrile (FIG. 2).

For preparation of EHT 1800, methyl ester 3 was saponified at 70° C. using KOH in MeOH:H₂O=10:1 to yield to the acid derivative 4. Coupling reaction for 1 hour at room temperature in DMF between acid 4 and phenylenediamine using BOP as coupling agent gave after purification EHT 1800 in 4% yield (FIG. 2).

Figure 3:
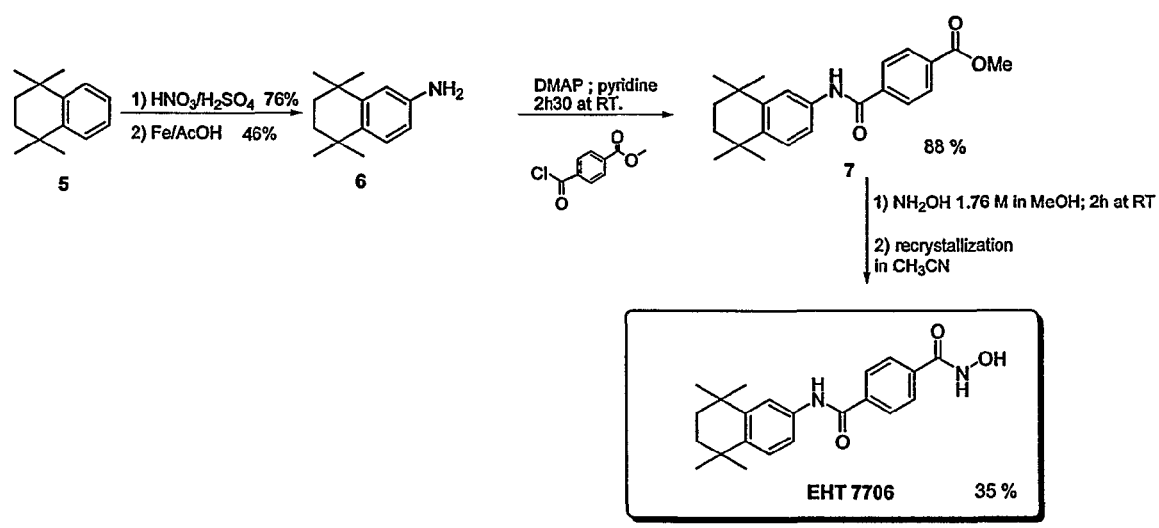

EHT 7706 were prepared from commercial 1,1,4,4-tetramethyltetrahydronaphtalene 5 (FIG. 3). Compound 5 was nitrated and reduced reacting successively with HNO₃/H₂SO₄ in 76% yield then with iron powder in acetic acid to led to the amino derivative 6 in 46% yield (previously described by Kagechika, H et al, *J. Med. Chem.*, 31, 2182-2192, 1988). Coupling reaction in pyridine with the acid chloride of terephthalic acid monomethyl ester (generated with thionyl chloride with a catalytic amount of DMF) afforded to methyl ester 7 in 88%. Methyl ester 7 was reacted with a solution of NH₂OH 1.76 M in MeOH for 2 hours at room temperature. Recrystallisation in acetonitrile led to EHT 7706 in 35% yield (FIG. 3).

Figure 4:
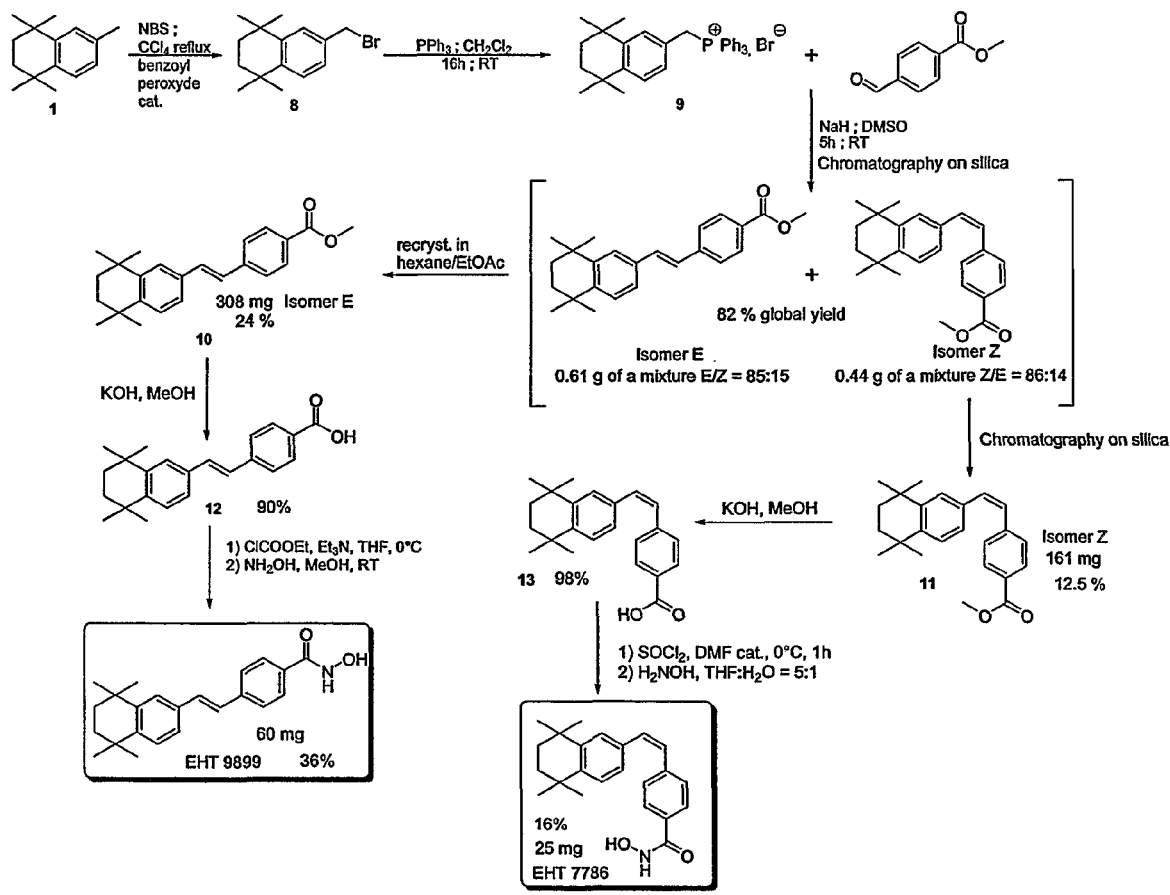

EHT 9899 and EHT 7786 were prepared from 1,1,4,4,6-pentamethyltetrahydronaphtalene 1 (FIG. 4). Compound 1 was brominated reacting with N-bromosuccinimide and a catalytic amount of benzoyl peroxide in carbon tetrachloride at reflux to give compound 8 in 84% yield.

The bromo derivative 8 reacted with triphenylphosphine in dichloromethane 16 h at room temperature to afford the corresponding phosphonium salt 9 in good yield. A Wittig reaction performed at room temperature in dimethylsulfoxyde between the phosphonium salt 9 and methyl-4-formylbenzoate, using NaH as base, afforded to a mixture of 2 isomers E and Z in 82% crude yield. After purification by column chromatography pure isomer E 10 is obtained in a 24% yield. Isomer Z 11 was obtained in pure form after two columns chromatography in 12.5% yield.

Pure isomer E 10 was saponified at 70° C. using KOH in MeOH:H₂O=10:1 to yield to the acid derivative 12 (previously described by Kagechika, H. et al., *J. Med. Chem.*, 32, 5, 1989, 1098-1108) which was reacted with ethyl chloroformate in THF at 0° C. in presence of triethylamine followed by addition of a solution of hydroxylamine in methanol to give to EHT 9899 (FIG. 4).

Pure isomer Z 11 was saponified at 70° C. using KOH in MeOH:H₂O=10:1 to yield to the acid derivative 13 (previously described by Kagechika, H. et al., *J. Med. Chem.*, 32, 5, 1989, 1098-1108) which was reacted at 0° C. with thionyl chloride in presence of a catalytic amount of DMF to give the acid chloride intermediate which reacted at room temperature with a solution of hydroxylamine in THF:H₂O=5:1 to yield to EHT 7786 (FIG. 4).

Figure 5:
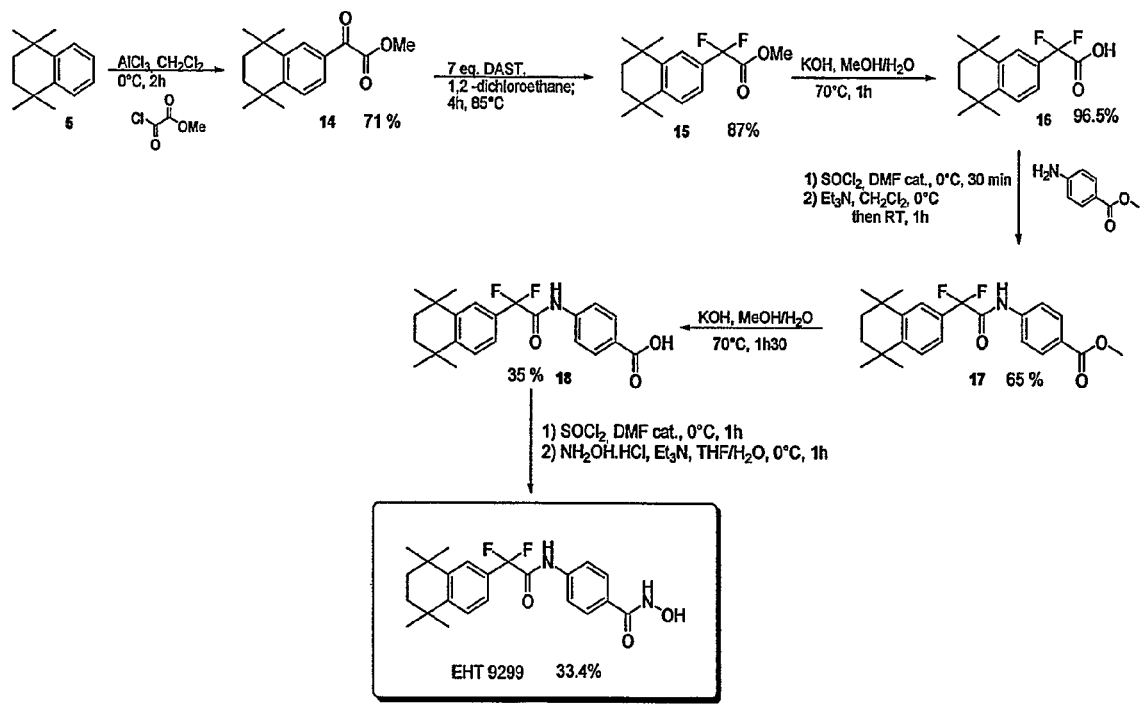

EHT 9299 was prepared in six steps from commercial 1,1,4,4-tetramethyltetrahydronaphtalene 5 (FIG. 5). Friedel-Craft acylation at 0° C. of 1,1,4,4-tetramethyltetrahydronaphtalene 5 with methyl oxalyl chloride in dichloromethane in presence of aluminium trichloride afforded to a-keto methylester 14. Fluorination of a-keto methylester 14 using 7 equivalents of diethylamino-sulphur trifluoride (DAST) in 1,2-dichloroethane at reflux led to the difluorinated compound 15 in 87% yield. Saponification of compound 15 at 70° C. using KOH in MeOH:H₂O=10:1 gave to the acid derivative 16. Coupling reaction between acid 16 and methyl-4-aminobenzoate using the acid chloride method afforded to the amide derivative 17 in 65% yield. Saponification of amide 17 at 70° C. using KOH in MeOH:H₂O=10:1 yielded to the acid derivative 18. Compound 18 reacted at 0° C. with thionyl chloride in presence of a catalytic amount of DMF to give the acid chloride intermediate which reacted at 0° C. with a solution of hydroxylamine in THF:H₂O=5:1 to yield to EHT 9299 (FIG. 5).

Figure 6:
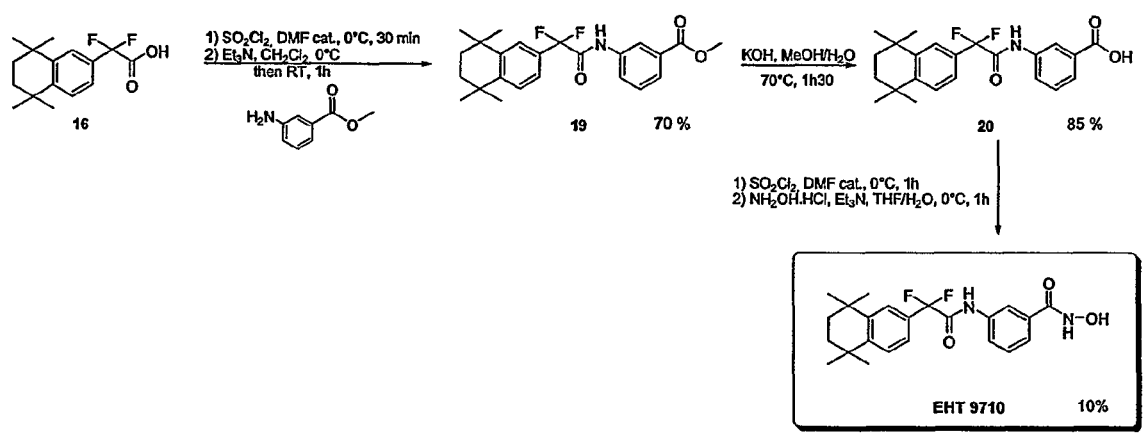

Similarly to EHT 9299, EHT 9710 was prepared in 3 steps starting from acid 16 (FIG. 6). Coupling reaction between acid 16 and methyl-3-aminobenzoate using the acid chloride method afforded to the amide derivative 19 in 70% yield. Saponification of amide 19 at 70° C. using KOH in MeOH:H₂O=10:1 yielded to the acid derivative 20. Acid 20 reacted at 0° C. with thionyl chloride in presence of a catalytic amount of DMF to give the acid chloride intermediate which reacted at 0° C. with a solution of hydroxylamine in THF:H₂O=5:1 to yield to EHT 9710 (FIG. 6).

Figure 7:
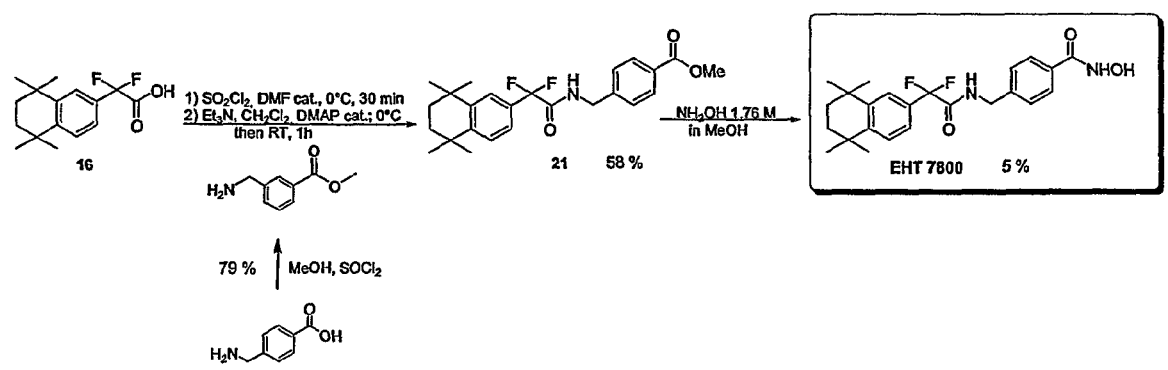

Similarly to EHT 9299, EHT 7800 was prepared from acid 16 (FIG. 7). Coupling reaction between acid 16 and methyl 4-(aminomethyl)benzoate using the acid chloride method afforded to the amide derivative 21 in 58% yield. The methyl ester amide 21 reacted with a solution of NH₂OH 1.76 M in MeOH to give to EHT 7800 in 5% yield after purification (FIG. 7).

Figure 8:
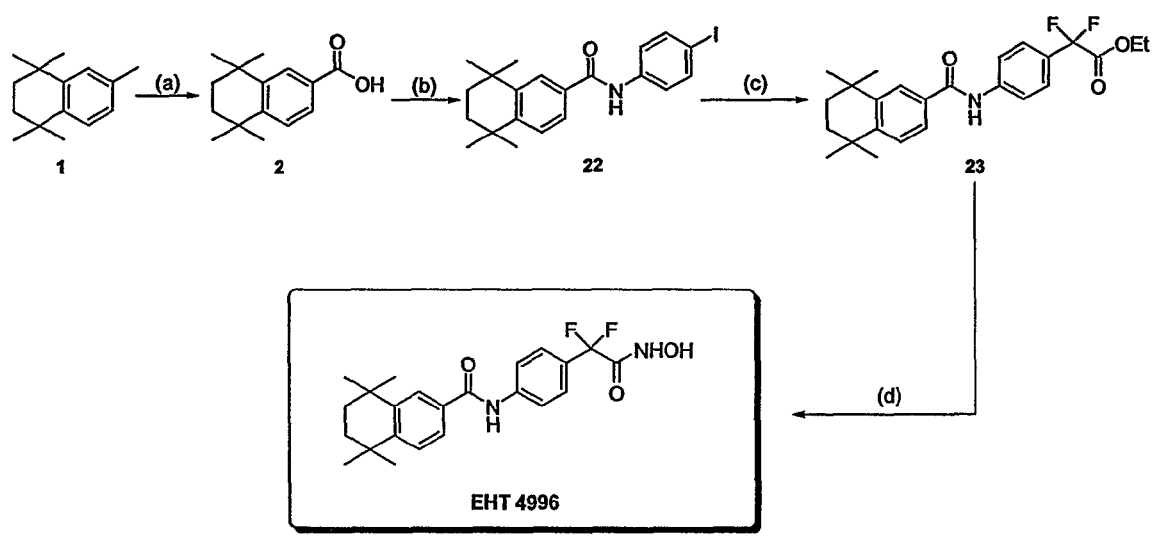

EHT 4996 was prepared in four steps from commercial 1,1,4,4,6-pentamethyltetrahydronaphtalene 1 (FIG. 8). Oxidation of compound 1 with potassium permanganate in presence of NaOH in pyridine at 95° C. for 16 h afforded the corresponding acid 2 in 67% yield. The acid 2 was coupled to 4-iodo-aniline in dichloromethane, using triethylamine as base and a catalytic amount of DMAP, via its acid chloride formation in SOCl₂ in presence of a catalytic amount of DMF, to yield to the iodo derivative 22. iodo derivative 22 was reacted with ethylbromodifluoroacetate in presence of copper powder at 58° C. in DMSO to led to the difluoro ethyl ester 23 in 75% yield. Ester 23 was treated with a solution of NH₂OH 1.76 M in MeOH at room temperature to lead to EHT 7706 in 35% yield (FIG. 8).

Figure 9:
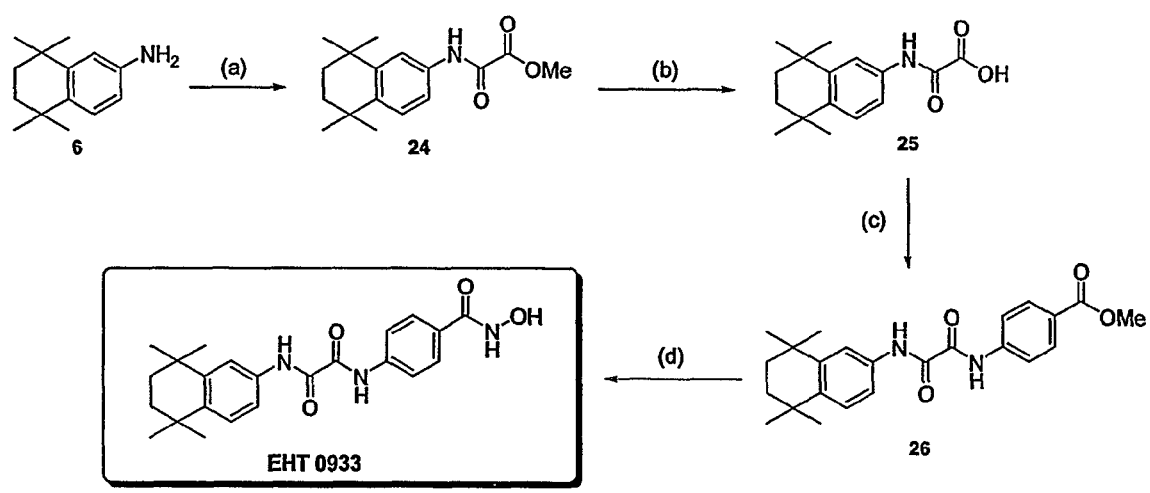

EHT 0933 was prepared in four steps from 5,6,7,8-tetrahydro-5,5,8,8-tetramethylnaphthalen-2-amine 6 (FIG. 9). 5,6,7,8-Tetrahydro-5,5,8,8-tetramethylnaphthalen-2-amine 6 was treated for 2 hours at room temperature with methoxyoxalylchloride in dichloromethane in presence of triethylamine as base to obtain the methyl ester 24. Methyl ester 24 was saponified for 3 hours at 70° C. using KOH in MeOH:H₂O=10:1 to yield to the oxalic acid derivative 25. The corresponding acid chloride of the oxalic acid derivative 25 was coupled for 2 hours at room temperature with methyl 4-aminobenzoate in dichloromethane in presence of triethylamine as base to give to methyl ester 26 in 27% yield. Finally ester 26 was treated with a solution of NH₂OH 1.76 M in MeOH for 3 hours at room temperature to lead to EHT 0933 in 30% yield (FIG. 9).

These methods for preparing compounds of formula (I) represent further objects of the present application.

It should be understood that other ways of producing these compounds may be designed by the skilled person, based on common general knowledge and following guidance contained in this application.

As indicated above, a further object of this invention relates to a pharmaceutical composition comprising at least one compound of formula (I), as defined above, and a pharmaceutically acceptable vehicle or support.

The compounds may be formulated in various forms, including solid and liquid forms, such as tablets, gel, syrup, powder, aerosol, etc.

The compositions of this invention may contain physiologically acceptable diluents, fillers, lubricants, excipients, solvents, binders, stabilizers, and the like. Diluents that may be used in the compositions include but are not limited to dicalcium phosphate, calcium sulphate, lactose, cellulose, kaolin, mannitol, sodium chloride, dry starch, powdered sugar and for prolonged release tablet-hydroxy propyl methyl cellulose (HPMC). The binders that may be used in the compositions include but are not limited to starch, gelatin and fillers such as sucrose, glucose, dextrose and lactose.

Natural and synthetic gums that may be used in the compositions include but are not limited to sodium alginate, ghatti gum, carboxymethyl cellulose, methyl cellulose, polyvinyl pyrrolidone and veegum. Excipients that may be used in the compositions include but are not limited to microcrystalline cellulose, calcium sulfate, dicalcium phosphate, starch, magnesium stearate, lactose, and sucrose. Stabilizers that may be used include but are not limited to polysaccharides such as acacia, agar, alginic acid, guar gum and tragacanth, amphotsics such as gelatin and synthetic and semi-synthetic polymers such as carbomer resins, cellulose ethers and carboxymethyl chitin.

Solvents that may be used include but are not limited to Ringers solution, water, distilled water, dimethyl sulfoxide to 50% in water, propylene glycol (neat or in water), phosphate buffered saline, balanced salt solution, glycol and other conventional fluids.

The dosages and dosage regimen in which the compounds of formula (I) are administered will vary according to the dosage form, mode of administration, the condition being treated and particulars of the patient being treated. Accordingly, optimal therapeutic concentrations will be best determined at the time and place through routine experimentation.

The compounds according to the invention can also be used enterally. Orally, the compounds according to the invention are suitable administered at the rate of 100 µg to 100 mg per day per kg of body weight. The required dose can be administered in one or more portions. For oral administration, suitable forms are, for example, tablets, gel, aerosols, pills, dragees, syrups, suspensions, emulsions, solutions, powders and granules; a preferred method of administration consists in using a suitable form containing from 1 mg to about 500 mg of active substance.

The compounds according to the invention can also be administered parenterally in the form of solutions or suspensions for intravenous or intramuscular perfusions or injections. In that case, the compounds according to the invention are generally administered at the rate of about 10 µg to 10 mg per day per kg of body weight; a preferred method of administration consists of using solutions or suspensions containing approximately from 0.01 mg to 1 mg of active substance per ml.

The compounds of formula (I) can be used in a substantially similar manner to other known anti-cancer agents for treating (both chemo preventively and therapeutically) various cancers or to other known agents for treating other diseases associated with abnormal cell proliferation, such as psoriasis, and also for treating central nervous system diseases, as specified above.

For the compounds of this invention, the dose to be administered, whether a single dose, multiple dose, or a daily dose, will of course vary with the particular compound employed because of the varying potency of the compound, the chosen route of administration, the size of the recipient, the type of disease (cancer, and in such a case optionally the type of tumours) and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. An oncologist skilled in the art of cancer treatment or a doctor skilled in the art for psoriasis, or central nervous system diseases treatment will be able to ascertain, without undue experimentation, appropriate protocols for the effective administration of the compounds of this present invention, such as by referring to the earlier published studies on compounds found to have, for instance, anti-cancer, anti-tumor, anti-psoriasis properties.

According to another aspect, the present invention relates to a method for the treatment of a disease associated with abnormal cell proliferation, and also central and peripheral nervous system diseases and neurodegenerative diseases associated with an excitotoxicity as identified above, comprising administering to a patient in need of such treatment an effective amount of at least one compound of general formula (I) as described above.

Preferred compounds for use according to the invention include any sub-group as defined above, and, as specific examples, the following compounds:

N-(4-(Hydroxycarbamoyl)phenyl)-5,6,7,8-tetrahydro-5,5,8,8-tetramethylnaphthalene-2-carboxamide EHT 3741

N-(4-(2-Aminophenylcarbamoyl)phenyl)-5,6,7,8-tetrahydro-5,5,8,8-tetramethyl-naphthalene-2-carboxamide EHT 1800

N-(1,2,3,4-Tetrahydro-1,1,4,4-tetramethylnaphthalen-6-yl)-N'-hydroxyterephthalamide EHT 7706

4-((E)-2-(1,2,3,4-tetrahydro-1,1,4,4-tetramethylnaphthalen-6-yl)vinyl)-N-hydroxybenzamide EHT 9899

4-((Z)-2-(1,2,3,4-tetrahydro-1,1,4,4-tetramethylnaphthalen-6-yl)vinyl)-N-hydroxybenzamide EHT 7786

4-(2,2-difluoro-2-(1,2,3,4-tetrahydro-1,1,4,4-tetramethylnaphthalen-7-yl)acetamido)-N-hydroxybenzamide EHT 9299

3-(2,2-difluoro-2-(1,2,3,4-tetrahydro-1,1,4,4-tetramethylnaphthalen-7-yl)acetamido)-N-hydroxybenzamide EHT 9710

4-((2,2-difluoro-2-(1,2,3,4-tetrahydro-1,1,4,4-tetramethylnaphthalen-7-yl)acetamido)methyl)-N-hydroxybenzamide EHT 7800

N-(4-((hydroxycarbamoyl)difluoromethyl)phenyl)-5,6,7,8-tetrahydro-5,5,8,8-tetramethylnaphthalene-2-carboxamide EHT 4996

N-(4-Hydroxycarbamoyl-phenyl)-N'-(5,5,8,8-tetramethyl-5,6,7,8-tetrahydro-naphthalen-2-yl)-oxalamide EHT 0933

A further object of this invention is the use of an effective amount of at least one compound of formula (I) as defined above for the preparation of pharmaceutical composition for the treatment of conditions mediated by HDACas identified above.

Because of their cell proliferation inhibitory activity, the compounds of this invention are suitable for treating a variety of diseases in a variety of conditions.

In this regard, "treatment" or "treating" includes both therapeutic and prophylactic treatments. Accordingly, the compounds may be used at very early stages of a disease, or before early onset, or after significant progression, including metastasis. The term "treatment" or "treating" designates in particular a reduction of the burden in a patient, such as a reduction in cell proliferation rate, a destruction of diseased proliferative cells, an inhibition of the formation of vessel or vessel-like structure, a reduction of tumor mass or tumor size, a delaying of tumor progression, as well as a complete tumor suppression.

Typical examples of diseases associated with abnormal cell proliferation include cancers and psoriasis, for instance. The compounds of this invention are particularly suited for the treatment of cancers, such as solid tumors or lymphoid tumors. Specific examples include promyelocytic leukaemia, prostate cancer, ovarian cancer, pancreas cancer, lung cancer, breast cancer, liver cancer, head and neck cancer, colon cancer, bladder cancer, non-Hodgkin's lymphoma cancer and melanoma.

The compounds may be administered according to various routes, typically by injection, such as local or systemic injection(s). Intratumoral injections are preferred for treating existing cancers. However, other administration routes may be used as well, such as intramuscular, intravenous, intradermic, subcutaneous, etc. Furthermore, repeated injections may be performed, if needed, although it is believed that limited injections will be needed in view of the efficacy of the compounds.

A further object of this invention is a composition for reducing cancer cell proliferation by administering in a subject having cancer an effective amount of compound of formula (I) as defined above.

A further object of this invention is a composition for treating metastatic cancers by administering in a subject in need of such treatment an effective amount of compound of formula (I) as defined above.

A further object of this invention is a composition for treating psoriasis by administering, preferably orally or topically (onto the skin), in a subject in need of such treatment an effective amount of compound of formula (I) as defined above.

A further object of this invention is a composition for treating Huntington's disease by administering in a subject in need of such treatment an effective amount of compound of formula (I) as defined above.

A further object of this invention is the use of a compound as defined above for the preparation of a pharmaceutical composition for treating metastatic cancers or for reducing cancer cell proliferation.

Without further elaboration, one skilled in the art can, based on the description herein, easily utilize the present described invention to its fullest extend. The following specific examples, which describe syntheses and biological testing of various compounds of the invention, are therefore, to be construed as merely illustrative, and not limitative of the remainder of the disclosure in any way whatsoever. All publications recited herein, including patents, are hereby incorporated by reference in their entirety.

LEGEND TO THE FIGURES

Figure 11:
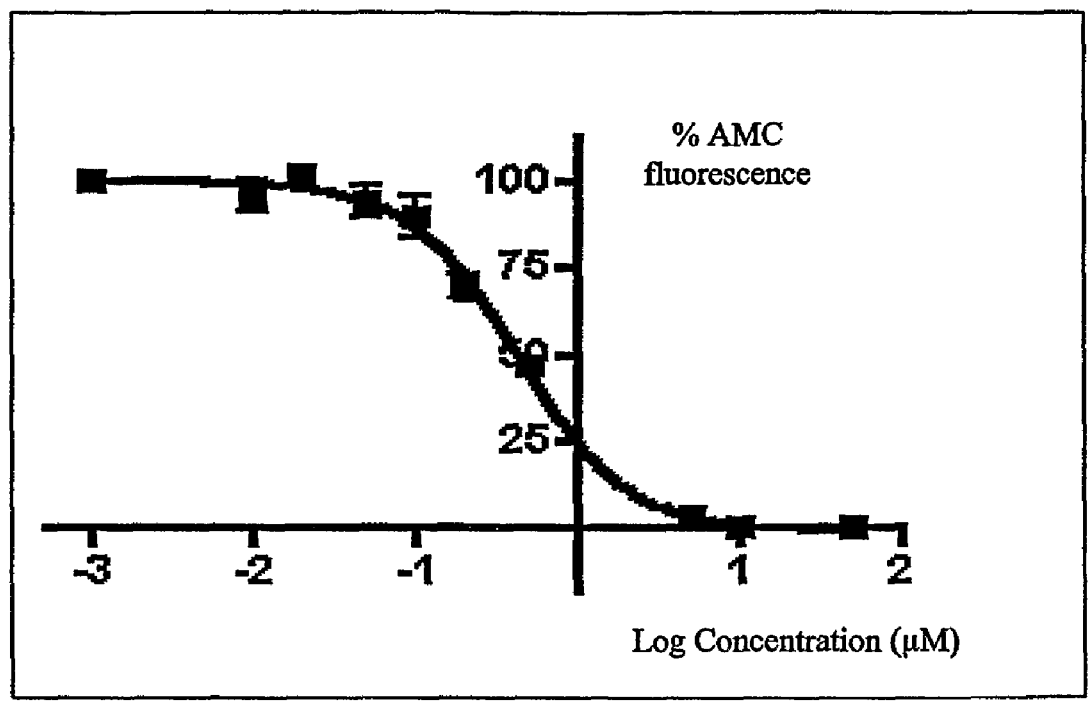

FIG. 1: Synthesis of SAHA EHT 0648 (reference compound)
FIG. 2: Synthesis of EHT 3741 and EHT 1800
FIG. 3: Synthesis of EHT 7706
FIG. 4: Synthesis of EHT 9899 and EHT 7786
FIG. 5: Synthesis of EHT 9299
FIG. 6: Synthesis of EHT 9710
FIG. 7: Synthesis of EHT 7800
FIG. 8: Synthesis of EHT 4996 ((a) KMnO$_4$, Pyridine, H$_2$O; 67% (b) 1. SOCl$_2$, DMF, O° C.; 2. 4-iodo-aniline, TEA, DMAP; 56%. (c) BrF$_2$CO$_2$Et, Cu, DMSO; 75%, (d) NH$_2$OH.HCl, KOH, MeOH; 97%).
FIG. 9: Synthesis of EHT 0933 ((a) Methyl oxalyl chloride, Et$_3$N, CH$_2$Cl$_2$; 90%, (b) KOH, MeOH, 3 h at 70° C.; 85% (c) i. SOCl$_2$, DMF cat., 0° C., ii. Methyl 4-aminobenzoate, Et$_3$N, CH$_2$Cl$_2$, 2 h at RT; 27% (d) NH$_2$OH.HCl, KOH, MeOH, 3 h at RT; 30%).
FIG. 10: IC$_{50}$ measurements for the positive controls HDAC inhibitor using Hela nuclear extract and the Fluor de Lys™ substrate. FIG. 10a, Trichostatin A (TSA). FIG. 10b, Suberoylanilide hydroxamic acid (SAHA).
FIG. 11: IC$_{50}$ measurements for EHT 9299 using Hela nuclear extract and the Fluor de Lys™ substrate.

EXAMPLES

The following are examples provided solely to illustrate the present invention and are not intended to limit the scope of the invention, as described herein.

General $^1$H NMR spectra were recorded at ambient temperature with an Avance 300 (Bruker) spectrometer. The compounds were analyzed by reverse phase high performance liquid chromatography (HPLC) using a Waters Autopurification System equipped with a Waters 2525 Pump, a Waters 2696 photodiode array detector, and a XTerra column (Part. No. 186000482, 5 µm, C18, 4.5×50 mm). The HPLC method used was a gradient of 5% solvent B to 100% in 7 min. Solvent A was H$_2$O with 0.05% TFA and solvent B was CH$_3$CN with 0.05% TFA (Method A). Melting points were measured with a Büchi B-545 melting point apparatus and are uncorrected. To isolate reaction products the solvent were removed by evaporation using a vacuum rotatory evaporator, the water bath temperature not exceeding 40° C.

Synthesis of N-hydroxy-N'-phenyloctanediamide (SAHA) EHT 0648 (Reference Compound)

Oxonane-2,9-dione
A solution of suberic acid (5.0 g, 28.7 mmol) in acetic anhydride (10 mL) was heated at reflux for 1 h. After cooling to RT, the solvent was removed in vacuo. The pale yellow residue was recrystallized from acetonitrile. After filtration and drying to the vacuum pump, the oxonane-2,9-dione was obtained as a white solid (2.26 g, 50.4% yield).

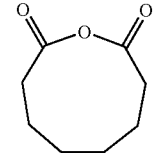

MW=156.18; Yield: 50.4%; White Solid; Mp (° C.)=51-52 (Litt. 69.4)

7-(Phenylcarbamoyl)heptanoic acid or suberanilic acid
Aniline (0.6 g, 6.4 mmol) was added at room temperature to a stirred solution of oxonane-2,9-dione (1.0 g, 6.4 mmol) in THF anhydrous. After stirring at RT for 0.5 h, the resulting mixture was diluted with water (100 mL). The formed white solid was filtered and collected. Purification by silica gel column chromatography using as eluent EtOAc:cyclohexane=80:20 to 100:0 afforded 7-(phenylcarbamoyl)heptanoic acid as a white solid (174 mg, 11% yield).
MW: 249.31; Yield: 11%; White Solid; Mp (° C.)=120 (Litt. 122-123).

N-Hydroxy-N'-phenyloctanediamide (SAHA) EHT 0648
To a solution of suberanilic acid (0.167 g, 0.67 mmol) in anhydrous THF (5 mL) were added successively via syringe at 0° C. ethyl chloroformate (85.2 □L, 0.89 mmol) and triethylamine (135.5 µl, 0.97 mmol) and the mixture was stirred at 0° C. for 10 min. The solid was filtered off and the filtrate was added to a freshly prepared hydroxylamine solution in MeOH (3.53 mL). Preparation of hydroxylamine solution in MeOH: A solution of hydroxylamine hydrochloride (0.22 g, 3.15 mmol) in MeOH (5 mL) was added to a stirred solution of KOH (0.18 g, 3.15 mmol) in MeOH (5 mL) at 0° C. After stirring for 0.25 h, the precipitate was removed and the 3.53 mL of filtrate was used as such. The resulting mixture was stirred at RT for 0.25 h and evaporated in vacuo. The residue was recrystallized twice from acetonitrile to obtain after drying (0.099 g, 56% yield) a white solid EHT 0648 N-hydroxy-N'-phenyloctanediamide (SAHA).

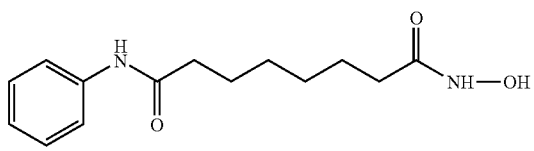

EHT 0648

MW: 264.32; Yield: 56%; White Solid; Mp (° C.)=161.4 (litt. 159-160.5° C.).

Example 1

N-(4-(Hydroxycarbamoyl)phenyl)-5,6,7,8-tetrahydro-5,5,8,8,-tetramethylnaphthalene-2-carboxamide EHT 3741

5,5,8,8-Tetramethyl-5,6,7,8-tetrahydro-naphthalene-2-carboxylic acid 2

A three neck round bottom flask (250 ml) equipped with a magnetic stirrer was charged with pyridine (37.5 mL), H$_2$O (12.5 ml) and NaOH (0.39 g, 9.8 mmol). 1,1,4,4,6-Pentamethyltetrahydronaphtalene 1 (1.00 g, 4.9 mmol) and KMnO$_4$ (3.12 g, 19.8 mmol) were added successively. The reaction mixture was stirred and heated at 95° C. for 16 h and cooled to 1° C. using an ice-water bath. HCl (6 N, 100 mL) was added to acidify to pH=1 and the product was extracted with EtOAc (5×100 mL), dried over Na$_2$SO$_4$, filtered to give after evaporation 5,5,8,8-tetramethyl-5,6,7,8-tetrahydro-naphthalene-2-carboxylic acid 2 (0.65 g, 57% yield) as a white solid.

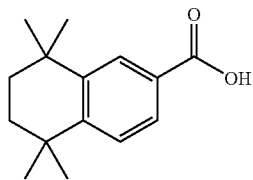

2

MW: 232.32; Yield 57%; White Solid; Mp (° C.): 196.2.
R$_f$: 0.4 (EtOAC:cyclohexane=25:75).
$^1$H NMR (CDCl$_3$, δ): 1.30 (s, 6H, 2×CH$_3$), 1.32 (s, 6H, 2×CH$_3$), 1.71 (s, 4H, 2×CH$_2$), 7.49 (d, 1H, J=8 Hz, ArH), 7.83 (dd, 1H, J=2 Hz, J=8 Hz, ArH), 8.08 (d, 1H, J=2 Hz, ArH), COOH not seen.
MS-ESI: m/z (rel. int.) 232.9 ([MH]$^+$, 100).
HPLC: Method A, detection 254 nm, RT=6.5 min, Peak area 99.0%.

Methyl 4-(5,6,7,8-tetrahydro-5,5,8,8-tetramethylnaphthalene-2-carboxamido)benzoate 3

5,5,8,8-Tetramethyl-5,6,7,8-tetrahydro-naphthalene-2-carboxylic acid 2 (0.20 g, 0.86 mmol) was dissolved in SOCl$_2$ (4.3 mL) at 0° C. A drop of DMF was added and the mixture was stirred for 0.5 h. The SOCl$_2$ was removed under vacuum and the crude acid chloride was dissolved in pyridine (10 mL). Methyl 4-aminobenzoate (0.143 g, 0.947 mmol) and DMAP (0.010 mg, 0.086 mmol) were added and the mixture was heated at 60° C. for 2 h with stirring. The mixture was poured into H$_2$O and the product was extracted with EtOAc; The organic layer was washed successively with HCl (2M), saturated NaHCO$_3$, saturated NaCl, dried over MgSO$_4$, filtrated to give after evaporation methyl 4-(5,6,7,8-tetrahydro-5,5,8,8-tetramethylnaphthalene-2-carboxamido)benzoate 3 (0.23 g, 73% yield) as a white solid.

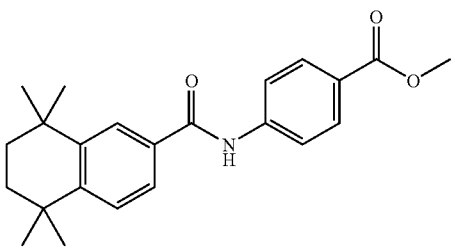

3

MW: 365.47; Yield 73%; White Solid; Mp (° C.): 206.
$^1$H NMR (CDCl$_3$, δ): 1.28 (s, 6H, 2×CH$_3$), 1.31 (s, 6H, 2×CH$_3$), 1.71 (s, 4H, 2×CH$_2$), 3.91 (s, 3H, OCH$_3$), 7.41 (d, 1H, J=8.2 Hz, ArH), 7.56 (dd, 1H, J=8.2 Hz, J=2.0 Hz, ArH), 7.74 (dd, 2H, J=7.0 Hz, J=1.7 Hz, ArH), 7.86 (d, 1H, J=2.0 Hz, ArH), 7.95 (s, 1H, NH), 8.05 (dd, 2H, J=6.9 Hz, J=1.7 Hz, ArH).
MS-ESI: m/z (rel. int.) 366.0 ([MH]$^+$, 100).
HPLC: Method A, detection 254 nm, RT=7.41 min, peak area 88.0%.

N-(4-(Hydroxycarbamoyl)phenyl)-5,6,7,8-tetrahydro-5,5,8,8-tetramethylnaphthalene-2-carboxamide EHT 3741

To a solution of methyl 4-(5,6,7,8-tetrahydro-5,5,8,8-tetramethylnaphthalene-2-carboxamido)benzoate 3 (0.200 g, 0.5 mmol) in MeOH (2 mL) was added an hydroxylamine solution (1.76 M, 2 mL) in MeOH and the reaction mixture was stirred 1 h at RT under magnetic stirring. The reaction mixture was adjusted to pH=5, concentrated and the residue was partitioned between EtOAc and H$_2$O. The organic layer was dried with Na$_2$SO$_4$ and the product was crystallized by dissolving the mixture at 80° C. in CH$_3$CN to give N-(4-(hydroxycarbamoyl)phenyl)-5,6,7,8-tetrahydro-5,5,8,8-tetramethylnaphthalene-2-carboxamide EHT 3741 (0.070 g, 35% yield) as a pale red solid.

Preparation of hydroxylamine solution (1.76 M) in MeOH: A solution of hydroxylamine hydrochloride (2.34 g, 33.7 mmol) in hot MeOH (12 mL) was added to a stirred solution of KOH (1.89 g, 33.7 mmol) in MeOH (7 mL). After stirring for 0.25 h the solution was cooled at 0° C. and the precipitate was removed by filtration.

17

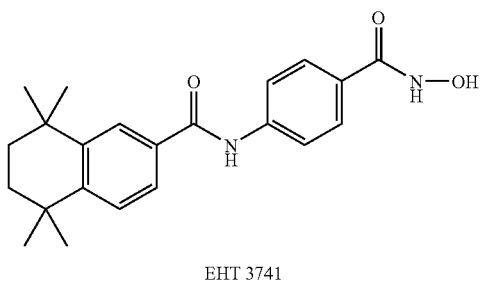

EHT 3741

MW: 366.50; Yield: 35%; Pale Red Solid; Mp (° C.): 240.5.
$R_f$: 0.35 (MeOH:CH$_2$Cl$_2$=5:95).
$^1$H-NMR (DMSO, δ): 1.27 (s, 6H, 2×CH$_3$), 1.30 (s, 6H, 2×CH$_3$), 1.67 (s, 4H, 2×CH$_2$), 7.48 (d, 1H, J=8.2 Hz, ArH), 7.65-7.90 (m, 6H, ArH), 8.98 (s, 1H, ArH), 10.29 (s, 1H, OH), 11.15 (s, 1H, NH).
MS-ESI m/z (rel. int.): 367.0 ([MH]$^+$, 100).
HPLC: Method A, detection UV 254 nm, EHT 3741 RT=6.1 min, peak area 98.7%.

Example 2

N-(4-(2-Aminophenylcarbamoyl)phenyl)-5,6,7,8-tetrahydro-5,5,8,8-tetramethyl-naphthalene-2-carboxamide EHT 1800

4-(5,6,7,8-tetrahydro-5,5,8,8-tetramethylnaphthalene-2-carboxamido)benzoic 4

A 25 mL round bottom flask equipped with a reflux condenser was charged with methyl methyl 4-(5,6,7,8-tetrahydro-5,5,8,8-tetramethylnaphthalene-2-carboxamido)benzoate 3 (0.200 g, 0.547 mmol), MeOH (10 mL) and KOH (0.122 g, 2.18 mmol). The reaction mixture was stirred for 16 h at reflux, evaporated to dryness and partitioned between EtOAc and H$_2$O. 6N HCl was added until pH became acidic and the organic layer was separated, washed with water, brine, dried with Na$_2$SO$_4$, filtered and concentrated on a rotary evaporator to give 4-(5,6,7,8-tetrahydro-5,5,8,8-tetramethylnaphthalene-2-carboxamido)benzoic acid 4 as a white solid (0.151 g, 78%).

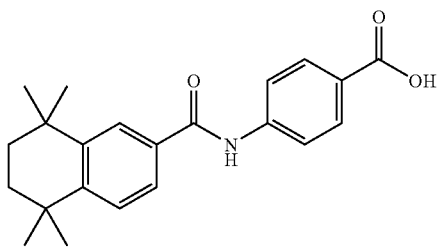

MW: 351.43; Yield 78%; white solid; Mp (° C.): 265.
$R_f$: 0.3 (EtOAc:Cyclohexane=50:50).
$^1$H NMR (CDCl$_3$, δ): 1.32 (s, 6H, 2×CH$_3$), 1.34 (s, 6H, 2×CH$_3$), 1.73 (s, 4H, 2×CH$_2$), 7.43 (d, 1H, J=8.53, ArH), 7.57 (d, 1H, J=8.25, J=1.98, ArH), 7.78 (d, 2H, J=8.74, ArH), 7.88 (d, 1H, J=8.74, ArH), 7.92 (s, 1H, NH), 8.13 (d, 2H, J=8.70, ArH), CO$_2$H not seen.
MS-ESI: m/z (rel. int.) 352.1 ([MH]$^+$, 100).
HPLC: Method A, detection 254 nm, RT=6.66 min, Peak area=96.3%.

18

N-(4-(2-Aminophenylcarbamoyl)phenyl)-5,6,7,8-tetrahydro-5,5,8,8-tetramethyl-naphthalene-2-carboxamide EHT 1800

To a solution of 4-(5,6,7,8-tetrahydro-5,5,8,8-tetramethyl-naphthalene-2-carboxamido)benzoic acid 4 (151 mg) in DMF 2 mL was added BOP (0.266 g), triethylamine (0.238 mL, 0.60 mmol) and phenylenediamine (0.093 g, 0.86 mmol). The reaction mixture was stirred 1 h at RT and diluted in EtOAc (25 mL), washed with NaH$_2$PO$_4$ (1M, 2×25 mL), brine (1M, 2×25 mL), NaHCO$_3$ (1M, 2×25 mL), brine (1M, 2×25 mL), dried over Na$_2$SO$_4$, filtered and concentrated to give an oil that was purified using silica gel chromatography with 40% [v/v] EtOAc in cyclohexane to give N-(4-(2-aminophenylcarbamoyl)phenyl)-5,6,7,8-tetrahydro-5,5,8,8-tetramethylnaphthalene-2-carboxamide EHT 1800 (8 mg, 4% yield) as a white solid.

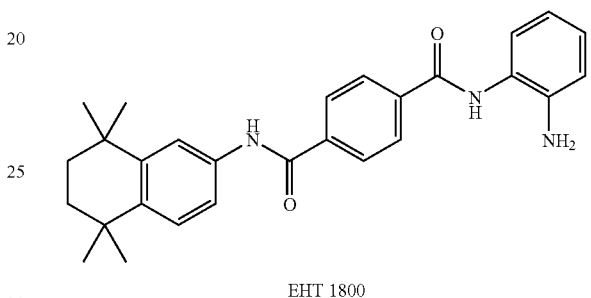

EHT 1800

MW: 441.36; Yield: 4%; White Solid; Mp (° C.): 215.9.
$R_f$: 0.55 (EtOAc:Cyclohexane=50:50).
$^1$H-NMR (DMSO, δ): 1.18 (s, 6H, 2×CH$_3$), 1.22 (s, 6H, 2×CH$_3$), 1.59 (s, 4H, 2×CH$_2$), 4.80 (s, 2H, NH$_2$), 6.50 (t, 1H, J=7.5 Hz, ArH), 6.69 (d, 1H, J=8.08 Hz, ArH), 6.87 (t, 1H, J=7.5 Hz, ArH), 7.07 (d, 1H, J=7.5 Hz, ArH), 7.40 (d, 1H, J=8.2 Hz, ArH), 7.63 6.50 (d, 1H, J=8.2 Hz, ArH), 7.79-7.81 (m, 3H, ArH), 7.90 (d, 2H, J=7.5 Hz, ArH), 9.51 (s, 1H, NH), 10.24 (s, 1H, NH).
MS-ESI m/z (rel. int.): 442.1 ([MH]$^+$, 40); 334.1 (100).
HPLC: Method A, detection UV 254 nm, EHT 1800 RT=5.83 min, peak area 97%.

Example 3

N-(1,2,3,4-Tetrahydro-1,1,4,4-tetramethylnaphthalen-6-yl)-N'-hydroxyterephthalamide EHT 7706

5,5,8,8-Tetramethyl-5,6,7,8-tetrahydro-naphthalen-2-ylamine 6

A mixture of HNO$_3$ [63%] (0.94 mL) and H$_2$SO$_4$ (1.5 mL) was added to 1,1,4,4-tetramethyl-1,2,3,4-tetrahydro-naphthalene 5 (2.0 g, 10.6 mmol) at −10° C. and the reaction mixture was stirred for 1 h. The reaction mixture was poured into ice:water and the product was extracted with CH$_2$Cl$_2$. The organic layer was washed with NaOH (1N), H$_2$O, brine, dried over MgSO$_4$ to give after solvent evaporation 1,1,4,4-tetramethyl-6-nitro-1,2,3,4-tetrahydro-naphthalene (1.87 g, 76%). ref. Kagechika, H., Kawachi, E., Hashimoto, Y., Shudo, K., Himi T., *J. Med. Chem.*, 31, 2182-2192, 1988. To a stirred solution of 1,1,4,4-tetramethyl-6-nitro-1,2,3,4-tetrahydro-naphthalene (0.593 g, 2.5 mmol) in glacial acetic acid (10 mL) was added iron powder (0.77, 13.8 mmol) over a period of 15 min. The reaction mixture was stirred at 60° C. for 3 hours. The volatiles were evaporated and the resulting oil was partitioned between EtOAc and water. Organics extracts were washed with brine, dried over MgSO₄ to obtain 5,5,8,8-tetramethyl-5,6,7,8-tetrahydro-naphthalen-2-ylamine 6 (0.232 g, 46% yield) as a brown solid.

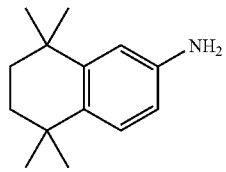

MW: 203.32; Yield: 35%; Brown Solid; Mp (° C.): 67.

¹H NMR (CDCl₃, δ): 1.23 (s, 6H, 2×CH₃), 1.25 (s, 6H, 2×CH₃), 1.64 (s, 4H, 2×CH₂), 3.50 (s, 2H, NH₂), 6.52 (dd, 1H, J=8.32 Hz, J=2.53 Hz, ArH), 6.63 (d, 1H, J=2.52 Hz, ArH), 7.10 (d, 1H, J=8.33 Hz, ArH).

MS-ESI: m/z (rel. int.) 204.0 ([MH]⁺, 100).

HPLC: Method A, detection 254 nm, RT=4.8 min, Peak area 90%.

N-(5,5,8,8-Tetramethyl-5,6,7,8-tetrahydro-naphthalen-2-yl)-terephthalamic acid methyl ester 7

Terephthalic acid monomethyl ester (194 mg, 1.08 mmol) was dissolved in SOCl₂ (5.39 mL) at 0° C. A drop of DMF was added and the mixture was stirred for 30 min. The SOCl₂ was removed under vacuum and the crude acid chloride was dissolved in pyridine (12.5 mL). 5,5,8,8-Tetramethyl-5,6,7,8-tetrahydro-naphthalen-2-ylamine 6 (200 g, 0.98 mmol) and DMAP (12 mg, 0.1 mmol) was added and the mixture was heated at 60° C. for 2 h with stirring. The mixture was poured into H₂O and the product was extracted with EtOAc. Them organic layer was washed successively with HCl 2M, saturated NaHCO₃, saturated NaCl, dried over MgSO₄ and filtrated to give after evaporation N-(5,5,8,8-tetramethyl-5,6,7,8-tetrahydro-naphthalen-2-yl)-terephthalamic acid methyl ester 7 (316 mg, 88% yield) as a white solid.

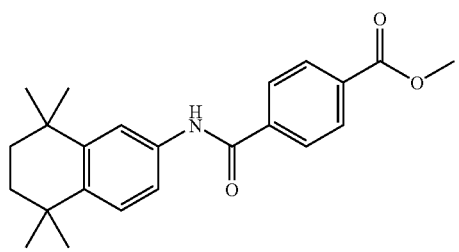

MW: 365.47; Yield 88%; White Solid; Mp: 211° C.

R_f: 0.9 (EtOAc:Cyclohexane=50:50).

¹H NMR (CDCl₃, δ): 1.28 (s, 6H, 2×CH₃), 1.30 (s, 6H, 2×CH₃), 1.70 (s, 4H, 2×CH₂), 3.96 (s, 3H, OCH₃), 7.32 (d, 1H, J=8.50 Hz, ArH), 7.45 (d, 1H, J=8.28 Hz, ArH), 7.53 (s, 1H, ArH), 7.80 (s, 1H, ArH), 7.92 (d, 2H, J=8.15 Hz, ArH), 8.14 (d, 2H, J=8.12 Hz, ArH).

MS-ESI: m/z (rel. int.) 366.0 ([MH]⁺, 100).

HPLC: Method A, detection 254 nm, RT=7.5 min, Peak area 90.6%.

N-(1,2,3,4-Tetrahydro-1,1,4,4-tetramethylnaphthalen-6-yl)-N'-hydroxyterephthalamide EHT 7706

To a solution of N-(5,5,8,8-tetramethyl-5,6,7,8-tetrahydro-naphthalen-2-yl)-terephthalamic acid methyl ester 7 (0.20 g, 0.55 mmol) in MeOH (2 mL) was added an hydroxylamine solution (1.76 M, 2 mL) in MeOH and the reaction mixture was stirred 1 h at room temperature under magnetic stirring. The reaction mixture was adjusted to pH=5, concentrated and the residue was partitioned between EtOAc and H₂O. The organic layer was dried with Na₂SO₄ and the product was crystallized by dissolving the mixture at 80° C. in CH₃CN to give N-(1,2,3,4-tetrahydro-1,1,4,4-tetramethylnaphthalen-6-yl)-N'-hydroxyterephthalamide EHT 7706 (0.05 g, 25% yield) as a white solid.

Preparation of hydroxylamine solution (1.76 M) in MeOH: A solution of hydroxylamine hydrochloride (2.34 g, 33.7 mmol) in hot MeOH (12 mL) was added to a stirred solution of KOH (1.89 g, 33.7 mmol) in MeOH (7 mL). After stirring for 0.25 h the solution was cooled at 0° C. and the precipitate was removed and the precipitate was removed by filtration.

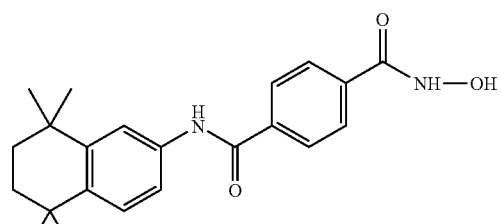

EHT 7706

MW: 366.50; Yield: 25%; White Solid; Mp (° C.): 230.2.

R_f: 0.4 (MeOH:CH₂Cl₂=5:95).

¹H-NMR (DMSO, δ): 1.14 (s, 6H, 2×CH₃), 1.15 (s, 6H, 2×CH₃), 1.55 (s, 4H, 2×CH₂), 7.19 (d, 1H, J=4.6 Hz, ArH), 7.49 (d, 1H, J=8.54, ArH), 7.58 (s, 1H, ArH), 7.78 (d, 2H, J=7.13, ArH), 7.91 (d, 2H, J=7.96 Hz, ArH), 9.08 (s, 1H, NH), 10.09 (s, 1H, OH), 11.29 (s, 1H, NH).

MS-ESI m/z (rel. int.): 367.0 ([MH]⁺, 100).

HPLC: Method A, detection UV 254 nm, EHT 7706 RT=6.1 min, peak area 99%.

Example 4

4-((E)-2-(1,2,3,4-tetrahydro-1,1,4,4-tetramethyl-naphthalen-6-yl)vinyl)-N-hydroxy-benzamide EHT 9899

6-(bromomethyl)-1,2,3,4-tetrahydro-1,1,4,4-tetramethyl-naphthalene 8

A solution of 1,2,3,4-tetrahydro-1,1,4,4,6-pentamethyl-naphthalene 1 (2.00 g, 9.88 mmol), N-bromosuccinimide (1.85 mmol, 10.37 mmol), benzoyl peroxide (91 mg, 0.28 mmol) in 35 mL of CCl₄ was heated at reflux (84° C., oil bath) for 2.5 h. After cooling top room temperature, the solution was concentrated in vacuo. Diethyl ether (100 mL) was added and the solution was filtered (to remove the succinimide formed) and concentrated to give a crude oil. The crude oil was purified by silica gel column chromatography using as eluent petroleum ether. 6-(Bromomethyl)-1,2,3,4-tetrahydro-1,1,4,4-tetramethylnaphthalene 8 (2.01 g, 72.5% yield) was obtained as a colourless oil.

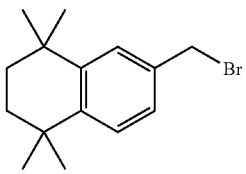

8

MW: 281.23; Yield: 72.5%; Colourless Oil.

$^1$H NMR (CDCl$_3$, δ): 1.27 (s, 6H, 2×CH$_3$), 1.28 (s, 6H, 2×CH$_3$), 1.67 (s, 4H, 2×CH$_2$), 3.77 (s, 2H, —CH$_2$Br), 7.16 (dd, 1H, J=8.1 Hz, J=2.0 Hz, ArH), 7.27 (d, 1H, J=8.1 Hz, ArH), 7.30 (d, 1H, J=2.0 Hz, ArH).

(5,6,7,8-Tetrahydro-5,5,8,8-tetramethyl-2-naphtalenyl)-methyl-triphenylphosphonium bromide 9

In a 250 mL round bottom flask was charged 6-(bromomethyl)-1,2,3,4-tetrahydro-1,1,4,4-tetramethylnaphthalene 8 (2.00 g, 7.11 mmol) in solution in 11 mL of dichloromethane. Triphenylphosphine (2.15 g, 8.18 mmol) was added via spatula at room temperature. The reaction mixture was stirred overnight at RT (16 h). Diethyl ether (200 mL) was added and the white precipitate formed was filtered and washed copiously with diethyl ether and dried in vacuo over P$_2$O$_5$. (5,6,7,8-tetrahydro-5,5,8,8-tetramethyl-2-naphtalenyl)-methyl-triphenylphosphonium bromide 9 (3.40 g, 88% yield) was obtained as a white solid.

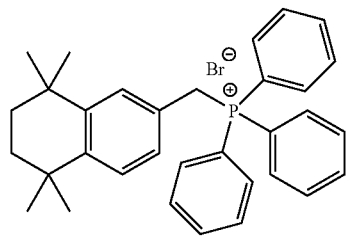

9

MW: 543.52; Yield: 88%; White Solid; Mp (° C.): 275.4.

$^1$H NMR (CDCl$_3$, δ): 1.29 (s, 6H, 2×CH$_3$), 1.33 (s, 6H, 2×CH$_3$), 1.70 (s, 4H, 2×CH$_2$), 3.92 (s, 3H, —OCH$_3$), 7.06 (d, 1H, J=16.3 Hz, HC=CH), 7.20 (d, 1H, J=16.3 Hz, HC=CH), 7.28-7.39 (m, 2H, ArH), 7.42 (s, 1H, ArH), 7.56 (d, 1H, J=8.4 Hz, ArH), 8.01 (d, 1H, J=8.4 Hz, ArH).

Methyl 4-((E)-2-(1,2,3,4-tetrahydro-1,1,4,4-tetramethyl-naphthalen-6-yl)vinyl)benzoate 10 and methyl 4-((Z)-2-(1,2,3,4-tetrahydro-1,1,4,4-tetramethylnaphthalen-6-yl)vinyl)benzoate 11.

In a 50 mL round bottom flask under nitrogen atmosphere equipped with a magnetic stirrer was charged (5,6,7,8-tetrahydro-5,5,8,8-tetramethyl-2-naphtalenyl)-methyl-triphenylphosphonium bromide 9 (2.00 g, 3.68 mmol) in 10 mL of DMSO. NaH (60% dispersion in oil, 155 mg, 3.86 mmol) was added portion wise at room temperature and the solution (became red) abandoned for 30 min. A solution of methyl-4-formylbenzoate (0.82 g, 5.00 mmol) in 7 mL of DMSO was added via syringe. The reaction which became pale yellow was abandoned for 5 h at room temperature. The reaction mixture is poured on ice water, a solution of HCl 1N (10 mL) was added and the solution was extracted with diethyl ether (3×150 mL). The organic layer was washed with brine (3×100 mL), dried over MgSO$_4$, filtered and evaporated to dryness. The crude product was incorporated on silica and purified by silica gel column chromatography using as eluent petroleum ether:EtOAc=100:0 to 99:1 to obtain BLE 04046A (0.444 g) which crystallized under vacuum and a white solid BLE 04046B (0.607 g). $^1$H NMR analysis of BLE 04046B revealed a mixture E:Z about 85:15 of methyl 4-(2-(1,2,3,4-tetrahydro-1,1,4,4-tetramethylnaphthalen-6-yl)vinyl)benzoate. BLE 04046B was recrystallized in hexane with a few drop of EtOAc to afford after filtration and drying pure methyl 4-((E)-2-(1,2,3,4-tetrahydro-1,1,4,4-tetramethylnaphthalen-6-yl)vinyl)benzoate 10 (0.308 g, % yield) as a white solid. BLE 04046A (0.444 g) was purified by silica gel column chromatography using as eluent petroleum ether:EtOAc=100:0 to 99:1 to obtain, after evaporation and drying, pure methyl 4-((Z)-2-(1,2,3,4-tetrahydro-1,1,4,4-tetramethylnaphthalen-6-yl)vinyl)benzoate 11 (0.161 g, 12.5% yield) as a colourless oil.

Methyl 4-((E)-2-(1,2,3,4-tetrahydro-1,1,4,4-tetramethyl-naphthalen-6-yl)vinyl)benzoate 10

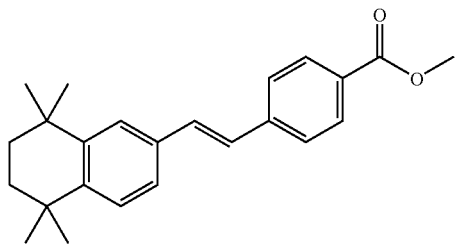

10

MW: 348.48; Yield 24%; White Solid; Mp (° C.): 166.5.

$^1$H NMR (CDCl$_3$, δ): 1.29 (s, 6H, 2×CH$_3$), 1.33 (s, 6H, 2×CH$_3$), 1.70 (s, 4H, 2×CH$_2$), 3.92 (s, 3H, —OCH$_3$), 7.06 (d, 1H, J=16.3 Hz, HC=CH), 7.20 (d, 1H, J=16.3 Hz, HC=CH), 7.28-7.39 (m, 2H, ArH), 7.42 (s, 1H, ArH), 7.56 (d, 2H, J=8.4 Hz, ArH), 8.01 (d, 2H, J=8.4 Hz, ArH).

Methyl 4-((Z)-2-(1,2,3,4-tetrahydro-1,1,4,4-tetramethyl-naphthalen-6-yl)vinyl)benzoate 11

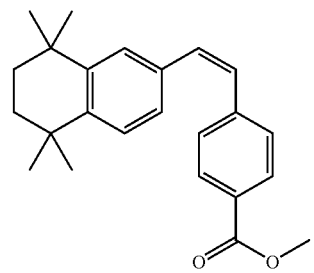

11

MW: 348.48; Yield 12.5%; Colourless Oil.

$^1$H NMR (CDCl$_3$, d): 1.09 (s, 6H, 2×CH$_3$), 1.25 (s, 6H, 2×CH$_3$), 1.63 (s, 4H, 2×CH$_2$), 3.90 (s, 3H, —OCH$_3$), 6.54 (d, 1H, J=12.3 Hz, HC=CH), 6.65 (d, 1H, J=12.3 Hz, HC=CH), 6.99 (dd, 1H, J=8.2 Hz, J=1.7 Hz, ArH), 7.14-7.21 (m, 2H, ArH), 7.36 (d, 2H, J=8.2 Hz, ArH), 7.90 (d, 2H, J=8.2 Hz, ArH).

4-((E)-2-(1,2,3,4-Tetrahydro-1,1,4,4-tetramethylnaphthalen-6-yl)vinyl)benzoic acid 12

In a 50 mL round bottom flask was charged methyl 4-((E)-2-(1,2,3,4-tetrahydro-1,1,4,4-tetramethylnaphthalen-6-yl)vinyl)benzoate 10 (0.30 g, 0.86 mmol) in 20 mL and water (2 mL) and KOH was added (193 mg, 3.44 mmol). The suspension was heated for 6 h at 70° C. Methanol was removed in vacuo, water (20 mL) was added and the solution washed with diethyl ether (2×30 mL). The aqueous solution was carefully acidified to pH=1 using a solution of HCl 1N and extracted with diethyl ether (3×100 ml). The organic layer was dried over MgSO₄, filtered and evaporated to yield to 4-((E)-2-(1,2,3,4-tetrahydro-1,1,4,4-tetramethylnaphthalen-6-yl)vinyl) benzoic acid 12 (0.26 g, 90% yield) as a white solid.

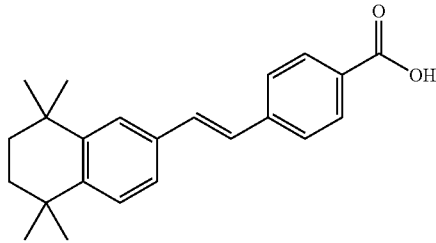

12

MW: 334.45; Yield 90%; White Solid; Mp (° C.): 273 (litt. 274-276).

$^1$H NMR (CDCl₃, δ): 1.24 (s, 6H, 2×CH₃), 1.29 (s, 6H, 2×CH₃), 1.65 (s, 4H, 2×CH₂), 7.20-7.45 (m, 4H, HC=CH and 2×ArH), 7.55 (s, 1H, ArH), 7.69 (d, 2H, J=8.2 Hz, ArH), 7.92 (d, 2H, J=8.2 Hz, ArH), —OH not seen.

4-((E)-2-(1,2,3,4-Tetrahydro-1,1,4,4-tetramethylnaphthalen-6-yl)vinyl)-N-hydroxybenzamide EHT 9899

To a solution of 4-((E)-2-(1,2,3,4-tetrahydro-1,1,4,4-tetramethylnaphthalen-7-yl)vinyl)benzoic acid 12 (0.16 g, 0.48 mmol) in anhydrous THF at 0° C. were added successively via syringe ethyl chloroformate (60.8 μL, 0.64 mmol) and triethylamine (96.3 μL, 0.69 mmol). The resulting mixture was stirred for 10 min at 0° C. The solid was filtered off and the filtrate was added to a freshly prepared solution of 2.5 mL of hydroxylamine in MeOH. Preparation of the hydroxylamine solution in MeOH: A solution of hydroxylamine hydrochloride (0.22 g, 3.15 mmol) in MeOH (5 mL) was added to a stirred solution of KOH (0.18 g, 3.15 mmol) in MeOH (5 mL) at 0° C. After stirring for 15 min, the precipitate was removed and 2.5 mL of filtrate was used as such. The resulting mixture was stirred at RT for 1.25 h and evaporated in vacuo. The crude product was incorporated on silica and purify by silica gel column chromatography using as eluent CH₂Cl₂:MeOH=99:1 to 99:2). After evaporation and drying to the vacuum pump a brown pale solid 4-((E)-2-(1,2,3,4-tetrahydro-1,1,4,4-tetramethylnaphthalen-6-yl)vinyl)-N-hydroxybenzamide EHT 9899 was obtained (0.06 g, 36% yield).

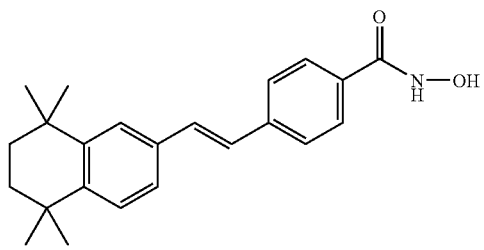

EHT 9899

MW: 349.47; Yield: 36%; Brown Pale Solid; Mp (° C.): 91.2.

$^1$H NMR (CDCl₃, δ): 1.29 (s, 6H, 2×CH₃), 1.32 (s, 6H, 2×CH₃), 1.70 (s, 4H, 2×CH₂), 7.13-7.45 (m, 3H, HC=CH and —NH—), 7.32 (s, 2H, ArH), 7.41 (s, 1H, ArH), 7.56 (d, 2H, J=5.2 Hz, ArH), 7.72 (s broad, 2H, ArH), 9.3 (s broad, 1H, OH).

MS-ESI m/z (rel. int.): 350.1 ([MH]⁺, 100).

HPLC: Method A, detection UV 254 nm, EHT 9899 RT=6.90 min, peak area 98.5%.

Example 5

4-((Z)-2-(1,2,3,4-tetrahydro-1,1,4,4-tetramethylnaphthalen-6-yl)vinyl)-N-hydroxy-benzamide EHT 7786

4-((Z)-2-(1,2,3,4-Tetrahydro-1,1,4,4-tetramethylnaphthalen-6-yl)vinyl)benzoic acid 13

In a 50 mL round bottom flask was charged methyl 4-((Z)-2-(1,2,3,4-tetrahydro-1,1,4,4-tetramethylnaphthalen-6-yl)vinyl)benzoate 11 (0.16 g, 0.46 mmol) in 15 mL and water (1.5 mL) and KOH was added (103 mg, 1.84 mmol). The suspension was heated for 6 h at 70° C. Methanol was removed in vacuo, water (20 mL) was added and the solution washed with diethyl ether (2×50 mL). The aqueous solution was carefully acidified to pH=1 using a solution of HCl 1N and extracted with diethyl ether (3×50 ml). The organic layer was dried over MgSO₄, filtered and evaporated to yield to 4-((Z)-2-(1,2,3,4-tetrahydro-1,1,4,4-tetramethylnaphthalen-6-yl)vinyl)benzoic acid 13 (0.151 g, 98% yield) as a white solid.

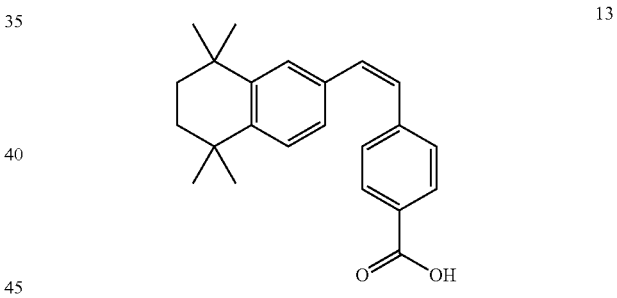

13

MW: 334.45; Yield 98%; White Solid.

$^1$H NMR (CDCl₃, δ): 1.08 (s, 6H, 2×CH₃), 1.25 (s, 6H, 2×CH₃), 1.63 (s, 4H, 2×CH₂), 6.54 (d, 1H, J=12.3 Hz, HC=CH), 6.65 (d, 1H, J=12.3 Hz, HC=CH), 6.99 (dd, 1H, J=8.1 Hz, J=1.7 Hz, ArH), 7.15-7.20 (m, 2H, ArH), 7.38 (d, 2H, J=8.1 Hz, ArH), 7.97 (d, 2H, J=8.1 Hz, ArH), COOH not seen.

MS-ESI: m/z (rel. int.) 335.1 ([MH]⁺, 100).

HPLC: Method A, detection 254 nm, RT=7.79 min, peak area=99.0%.

4-((Z)-2-(1,2,3,4-Tetrahydro-1,1,4,4-tetramethylnaphthalen-6-yl)vinyl)-N-hydroxybenzamide EHT 7786

To a solution of 4-((Z)-2-(1,2,3,4-tetrahydro-1,1,4,4-tetramethylnaphthalen-7-yl)vinyl)benzoic acid 13 (0.15 g, 0.45 mmol) in thionyl chloride (2.5 mL) was added at 0° C. two drops of DMF and the reaction mixture was abandoned 1 h at 0° C. under magnetic stirring. This solution was evaporated in vacuo, CH₂Cl₂ was added (10 mL) and the solution was again evaporated. To a solution of H₂NOH.HCl (1.38 g, 20 mmol) in 17.24 mL of THF and 3.45 mL of water (THF:H₂O=5:1) was added at 0° C. Et₃N (3.45 mL, excess). This mixture was kept 1 h at 0° C. The acid chloride formed was dissolved in CH$_2$Cl$_2$ (7.14 mL) and added slowly drop wise to the freshly prepared solution of NH$_2$OH in THF:H$_2$O at 0° C. The reaction mixture was stirred at room temperature overnight and evaporated to dryness. The crude product was incorporated on silica and purify by silica gel column chromatography using as eluent CH$_2$Cl$_2$:MeOH=99:1 to 99:2). After evaporation and drying to the vacuum pump a brown pale solid 4-((Z)-2-(1,2,3,4-tetrahydro-1,1,4,4-tetramethylnaphthalen-6-yl)vinyl)-N-hydroxybenzamide EHT 7786 was obtained (0.10 g, 64% yield).

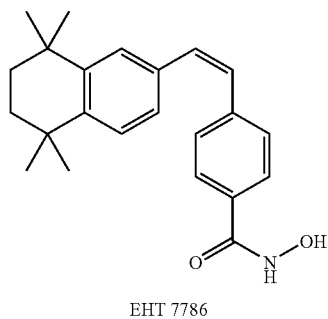

EHT 7786

MW: 349.47; Yield: 64%; Brown Pale Solid; Mp (° C.): 112.9.

$^1$H-NMR (CDCl$_3$, δ): 1.08 (s, 6H, 2×CH$_3$); 1.24 (s, 6H, 2×CH$_3$); 1.62 (s, 4H, 2×CH$_2$); 6.47 (d, 1H, J=12.3 Hz, —HC═CH—); 6.60 (d, 1H, J=12.3 Hz, —HC═CH—); 6.96 (dd, 1H, J=7.9 Hz, J=1.5 Hz, ArH); 7.14 (d, 1H, J=1.5 Hz, ArH); 7.15 (d, 1H, J=7.8 Hz, ArH); 7.31 (d, 2H, J=5.7 Hz, ArH); 7.58 (d, 2H, J=5.7 Hz, ArH); OH and NH not seen.

MS-ESI m/z (rel. int.): 350.1 ([MH]$^+$, 100).

HPLC: Method A, detection UV 254 nm, EHT 7786 RT=6.83 min, peak area 99.0%.

Example 6

4-(2,2-difluoro-2-(1,2,3,4-tetrahydro-1,1,4,4-tetramethylnaphthalen-7-yl)acetamido)-N-hydroxybenzamide EHT 9299

Methyl 2-(1,2,3,4-tetrahydro-1,1,4,4-tetramethylnaphthalen-6-yl)-2-oxoacetate 14

1,1,4,4-Tetramethyl-1,2,3,4-tetrahydro-naphthalene 5 (2.0 g, 10.6 mmol) was dissolved in dichloromethane (4 mL). The solution was frozen at 0° C., and aluminium trichloride (1.56 g, 11.7 mmol) was added. The mixture was stirred at 0° C. under nitrogen atmosphere. Methyl oxalyl chloride (1.08 mL, 11.7 mmol) was added via syringe. The black mixture was stirred at 0° C. for 2 h. While stirring at room temperature, ice (20 g) was added then slowly concentrated HCl (2 mL). The product was extracted with CH$_2$Cl$_2$ (5×50 mL). The organic layer was washed with brine (3×20 mL), dried over MgSO$_4$, filtered and evaporated in vacuo. The crude product was purified by chromatography on silica using as eluent cyclohexane:EtOAc=98:02. Methyl 2-(1,2,3,4-tetrahydro-1,1,4,4-tetramethylnaphthalen-6-yl)-2-oxoacetate 14 (2.05 g, 71% yield) was obtained as a yellow oil.

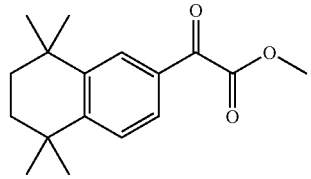

14

MW: 274.35; Yield: 71%; Yellow Oil.

R$_f$: 0.35 (cyclohexane:EtOAc=98:02).

$^1$H-NMR (CDCl$_3$, δ): 1.30 (s, 6H, 2×CH$_3$), 1.31 (s, 6H, 2×CH$_3$), 1.71 (s, 4H, 2×CH$_2$), 3.97 (s, 3H, OMe), 7.43 (d, 1H, J=8.3 Hz, ArH), 7.71 (dd, 1H, J=8.3 Hz, J=1.9 Hz, ArH), 8.00 (d, 1H, J=1.9 Hz, ArH)

$^{13}$C-NMR (CDCl$_3$, δ): 183.70, 162.12, 151.00, 143.71, 127.64, 126.30, 125.01, 124.99, 50.27, 32.70, 32.41, 32.31, 32.19, 29.44.

MS-ESI m/z (rel. int.): 297 ([M+Na]$^+$, 5), 215. (100).

HPLC: Method A, detection UV 254 nm, RT=7.45 min, peak area 93.78%.

Methyl 2,2-difluoro-2-(1,2,3,4-tetrahydro-1,1,4,4-tetramethylnaphthalen-6-yl)acetate 15

Methyl 2-(1,2,3,4-tetrahydro-1,1,4,4-tetramethylnaphthalen-6-yl)-2-oxoacetate 14 (1.47 g, 5.36 mmol) was dissolved in dichloroethane (22.05 mL). Diethylamino-sulfur trifluoride (DAST, 3.51 mL, 26.79 mmol) was added via syringe at RT. The black mixture was stirred at 85° C. for 4 h. DAST (1.3 mL, 10.72 mmol) was added via syringe. The mixture was stirred at 85° C. for 5.5 h. The mixture was evaporated in vacuo. The crude product was purified by chromatography on silica using as eluent cyclohexane:EtOAc=98:02. Methyl 2,2-difluoro-2-(1,2,3,4-tetrahydro-1,1,4,4-tetramethylnaphthalen-6-yl)acetate 15 was obtained (1.38 g, 86.8% yield) as a yellow oil.

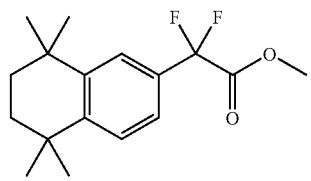

15

MW: 296.35; Yield: 86.8%; Yellow Oil.

R$_f$: 0.45 (cyclohexane:EtOAc=98:02).

$^1$H-NMR (CDCl$_3$, δ): 1.27 (s, 6H, 2×CH$_3$), 1.28 (s, 6H, 2×CH$_3$), 1.69 (s, 4H, 2×CH$_2$), 3.79 (s, 3H, OMe), 7.30-7.40 (m, 2H, ArH), 7.54 (s, 1H, ArH).

2,2-Difluoro-2-(1,2,3,4-tetrahydro-1,1,4,4-tetramethyl-naphthalen-6-yl)acetic acid 16

Methyl 2,2-difluoro-2-(1,2,3,4-tetrahydro-1,1,4,4-tetramethylnaphthalen-6-yl)acetate 15 (1.38 g, 4.65 mmol) was dissolved in methanol (129 mL). Water (12.9 mL) and NaOH (1.04 g, 18.57 mmol) were successively added at RT. The mixture was stirred at 70° C. for 1 h. The mixture was evaporated in vacuo. The crude product was dissolved in water and extracted with diethyl ether (2×50 mL). The aqueous layer was acidified by HCl (1M) to about pH=1 and extracted with diethyl ether (3×100 mL). The organic layer was dried over MgSO$_4$, filtered and evaporated to obtain 2,2-difluoro-2-(1,2,3,4-tetrahydro-1,1,4,4-tetramethylnaphthalen-6-yl)acetic acid 16 (1.27 g, 96.5% yield) as an orange solid.

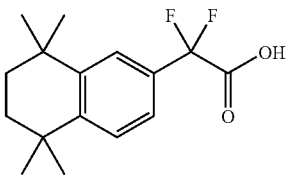

16

MW: 282.35; Yield: 96.5%; Orange Solid; Mp (° C.): 136.8.

¹H-NMR (CDCl₃, δ): 1.27 (s, 6H, 2×CH₃), 1.28 (s, 6H, 2×CH₃), 1.68 (s, 4H, 2×CH₂), 7.30-7.40 (m, 2H, ArH), 7.55 (s, 1H, ArH), 8.75 (s, 1H, COOH).

Methyl 4-(2,2-difluoro-2-(1,2,3,4-tetrahydro-1,1,4,4-tetramethylnaphthalen-6-yl)acetamido)benzoate 17

2,2-Difluoro-2-(1,2,3,4-tetrahydro-1,1,4,4-tetramethylnaphthalen-6-yl)acetic acid 16 (0.70 g, 2.48 mmol) was dissolved in SOCl₂ and two drops of DMF were added at 0° C. This mixture was stirred at 0° C. for 30 min and evaporated in vacuo. The resulting acid chloride was dissolved in CH₂Cl₂ (5 mL). Methyl-4-aminobenzoate (0.38 g, 2.48 mmol) and DMAP (30 mg, 0.25 mmol) were dissolved in CH₂Cl₂ (5 mL) and Et₃N (2.9 mL) was added at 0° C. The solution of the acid chloride in CH₂Cl₂ was added and this mixture stirred for 10 min at 0° C. and then abandoned to RT for 1 h. A solution of aqueous NH₄Cl 5% was added (200 mL) and the mixture was extracted with EtOAc (3×100 mL). The organic layer was washed with aqueous NaHCO₃ 5% (2×20 mL), brine (2×20 mL), dried over MgSO₄, filtered and evaporated in vacuo. The crude product was purified by chromatography on silica using as eluent cyclohexane:EtOAc=9:1. After evaporation, methyl 4-(2,2-difluoro-2-(1,2,3,4-tetrahydro-1,1,4,4-tetramethylnaphthalen-6-yl)acetamido)benzoate 17 (0.67 g, 65% yield) was obtained as a beige solid.

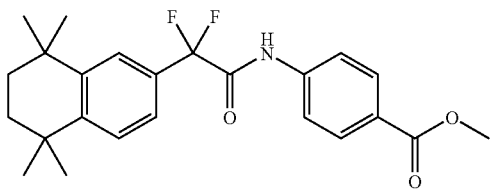

17

MW: 415.47; Yield: 65%; Beige Solid; Mp (° C.): 108 (dec.).

R_f: 0.40 (cyclohexane:EtOAc=90:10).

¹H-NMR (CDCl₃, δ): 1.21 (s, 6H, 2×CH₃), 1.26 (s, 6H, 2×CH₃), 1.66 (s, 4H, 2×CH₂), 3.86 (s, 3H, OMe), 7.30-7.40 (m, 2H, ArH), 7.61 (d, 1H, J=2.0 Hz, ArH), 7.71 (d, 2H, J=9.0 Hz, ArH), 7.71 (d, 2H, J=9.0 Hz, ArH), 8.93 (s, 1H, NH).

MS-ESI m/z (rel. int.): 416.1 ([MH]⁺, 65), 396.1 (90), 150.0 (100).

HPLC: Method A, detection UV 254 nm, RT=7.75 min, peak area 97%.

4-(2,2-Difluoro-2-(1,2,3,4-tetrahydro-1,1,4,4-tetramethylnaphthalen-6-yl)acetamido)benzoic acid 18

4-[2,2-Difluoro-2-(5,5,8,8-tetramethyl-5,6,7,8-tetrahydro-naphthalen-2-yl)-acetylamino]-benzoic acid methyl ester 17 (500 mg, 1.20 mmol) was dissolved in methanol (33.5 mL). Water (3.35 mL) and NaOH (270 mg, 4.81 mmol) were successively added at RT. The mixture was stirred at 70° C. for 1 h. The mixture was evaporated in vacuo and dissolved in water (100 ml) and extracted with diethyl ether (2×50 mL). The aqueous layer was acidified by HCl (1M) to about pH=1 and extracted with diethyl ether (2×100 mL), the organic layer was dried over MgSO₄, filtered and evaporated. 4-(2,2-Difluoro-2-(1,2,3,4-tetrahydro-1,1,4,4-tetramethylnaphthalen-6-yl)acetamido)benzoic acid 18 was obtained (169 mg, 35% yield) as a beige solid.

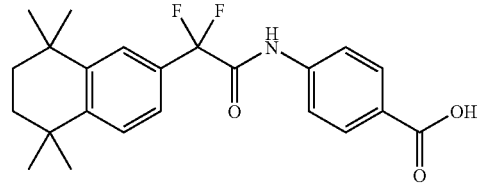

18

MW: 401.46; Yield: 35%; Beige Solid.

¹H-NMR (CD₃OD, δ): 1.29 (s, 6H, 2×CH₃), 1.30 (s, 6H, 2×CH₃), 1.73 (s, 4H, 2×CH₂), 7.37-7.50 (m, 2H, ArH), 7.65 (s, 1H, ArH), 7.75 (d, 2H, J=8.3 Hz, ArH), 8.00 (d, 2H, J=8.3 Hz, ArH), OH and NH exchanged.

4-(2,2-Difluoro-2-(1,2,3,4-tetrahydro-1,1,4,4-tetramethylnaphthalen-7-yl)acetamido)-N-hydroxybenzamide EHT 9299

A) 4-[2,2-Difluoro-2-(5,5,8,8-tetramethyl-5,6,7,8-tetrahydro-naphthalen-2-yl)-acetylamino]-benzoic acid 18 (170 mg, 0.425 mmol) was dissolved in SOCl₂ (2.4 mL) and two drops of DMF were added at 0° C. The mixture was stirred at 0° C. for 1 h and evaporated and the crude product was dissolved in CH₂Cl₂ (5 mL). B) Hydroxylamine hydrochloride (1.38 g, 20 mmol) was dissolved in THF (17.2 mL) and water (3.45 mL) and Et₃N (3.45 mL) at 0° C., the mixture was stirred at 0° C. for 1 h. A was added in B at 0° C. and this mixture was stirred at 0° C. for 10 min and at RT for 17.75 h. The mixture was evaporated and water was added (50 ml) before to be extracted with CH₂Cl₂ (3×50 mL). The organic layer was washed with brine (2×20 mL) and dried with MgSO₄, filtered and evaporated. The crude product was purified by column chromatography using as eluent cyclohexane:AcOEt=99:1. 4-(2,2-Difluoro-2-(1,2,3,4-tetramethylnaphthalen-7-yl)acetamido)-N-hydroxybenzamide EHT 9299 was obtained (58.3 mg, 33.4% yield) as a pink solid.

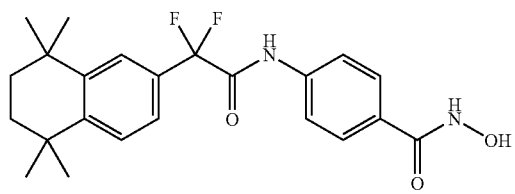

EHT 9299

MW: 416.46; Yield: 33%; Pink Solid; Mp (° C.): 120.4 (dec.).

R_f: 0.15 (cyclohexane:EtOAc=99:1).

¹H-NMR (CD₃OD, δ): 1.19 (s, 6H, 2CH₃), 1.20 (s, 6H, 2CH₃), 1.62 (s, 4H, 2CH₂), 7.32-7.37 (dd, 2H, J=8.2 Hz, J=8.4 Hz, ArH), 7.54 (s, 1H, ArH), 7.65 (s, 4H, ArH), 2×NH and OH exchanged.

MS-ESI m/z (% rel. int.): 417 (47.28, [MH]⁺).

HPLC: Method A, detection UV 254 nm, EHT 9299 RT=6.30 min, peak area 95.39%.

Example 7

3-(2,2-difluoro-2-(1,2,3,4-tetrahydro-1,1,4,4-tetramethylnaphthalen-7-yl)acetamido)-N-hydroxybenzamide EHT 9710

Methyl 3-(2,2-difluoro-2-(1,2,3,4-tetrahydro-1,1,4,4-tetramethylnaphthalen-6-yl)acetamido)benzoate 19

A) 2,2-Difluoro-2-(1,2,3,4-tetrahydro-1,1,4,4-tetramethylnaphthalen-6-yl)acetic acid 16 (0.53 g, 1.88 mmol) was dissolved in $SOCl_2$ and two drops of DMF were added at 0° C. The mixture was stirred at 0° C. for 0.5 h, evaporated and the crude product was dissolved in $CH_2Cl_2$ (5 mL). B) Methyl-3-aminobenzoate (284 mg, 1.88 mmol) and DMAP (23 mg, 0.19 mmol) were dissolved in $CH_2Cl_2$ (5 mL) and $Et_3N$ (2.6 mL) was added at 0° C. A) was added in B) at 0° C. and this mixture was stirred at 0° C. for 10 min and abandoned at RT for 1 h. The mixture was poured in aqueous $NH_4Cl$ 5% (100 mL) and extracted with EtOAc (3×50 mL). The organic layer was washed with $NaHCO_3$ (2×100 mL), brine (2×100 mL), dried with $MgSO_4$, filtered and evaporated. The crude product was purified by column chromatography using as eluent cyclohexane:EtOAc=90:10. Methyl 3-(2,2-difluoro-2-(1,2,3,4-tetrahydro-1,1,4,4-tetramethylnaphthalen-6-yl)acetamido)benzoate 19 was obtained (0.55 g, 70% yield) as a yellow oil.

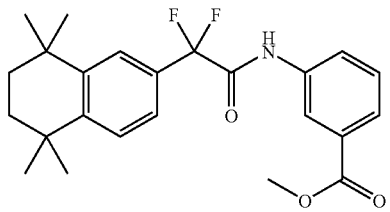

19

MW: 415.47; Yield: 69.9%; Yellow Oil.
$R_f$: 0.40 (cyclohexane:EtOAC=90:10).
$^1$H-NMR ($CDCl_3$, δ): 1.27 (s, 6H, 2×$CH_3$), 1.29 (s, 6H, 2×$CH_3$), 1.69 (s, 4H, 2×$CH_2$), 3.91 (s, 3H, $CH_3$), 7.39 (s, 2H, ArH), 7.43 (t, 1H, J=8.0 Hz, ArH), 7.60 (s, 1H, ArH), 7.85 (dd, 1H, J=1.0 Hz, J=8.1 Hz, ArH), 7.95 (d, 1H, J=8.1 Hz, ArH), 8.14 (d, 1H, J=1.3 Hz, ArH), 8.30 (s, 1H, NH).
MS-ESI m/z (rel. int.): 416 ([MH]$^+$, 100).
HPLC: Method A, detection UV 254 nm, RT=7.73 min, peak area 97.1%.

3-(2,2-Difluoro-2-(1,2,3,4-tetrahydro-1,1,4,4-tetramethylnaphthalen-6-yl)acetamido)benzoic acid 20

Methyl 3-(2,2-difluoro-2-(1,2,3,4-tetrahydro-1,1,4,4-tetramethylnaphthalen-6-yl)acetamido)benzoate 19 (0.50 g, 1.20 mmol) was dissolved in methanol (33.5 mL). Water (3.35 mL) was added via syringe at RT and KOH (0.27 g, 4.81 mmol) was added. The reaction mixture was heated at 70° C. for 2 h. After cooling to RT the mixture was evaporated in vacuo. The crude product was dissolved in water (30 mL) and extracted with ether (2×50 mL). The aqueous layer was acidified by a solution of HCl 1M to about pH=1. The aqueous layer was extracted with ether (2×100 mL), dried over $MgSO_4$, filtered and evaporated. The crude product was purified by column chromatography using as eluent cyclohexane: EtOAc=98:02. 3-(2,2-Difluoro-2-(1,2,3,4-tetrahydro-1,1,4,4-tetramethylnaphthalen-6-yl)acetamido)benzoic acid 20 was obtained (0.41 g, 84% yield) as an orange solid.

MW: 401.44; Yield: 84.4%; Orange Solid; Mp (° C.): 103.9 (dec.).
$R_f$: 0.45 (cyclohexane:EtOAc=98:02).
$^1$H-NMR ($CDCl_3$, δ): 1.27 (s, 6H, 2×$CH_3$), 1.29 (s, 6H, 2×$CH_3$), 1.68 (s, 4H, 2×$CH_2$), 7.39 (s, 1H, ArH), 7.44 (t, 1H, J=8.0 Hz, ArH), 7.57 (s, 1H, ArH), 7.61 (s, 1H, ArH), 7.88 (d, 1H, J=8.2 Hz, ArH), 8.02 (d, 1H, J=8.1 Hz, ArH), 8.14 (s, 1H, ArH), 8.34 (s, 1H, NH), 10.1 (s, 1H, OH).
MS-ESI m/z (rel. int.): 401.9 ([MH]$^+$, 100).
HPLC: Method A, detection UV 254 nm, RT=6.92 min, peak area 96.31%.

3-(2,2-Difluoro-2-(1,2,3,4-tetrahydro-1,1,4,4-tetramethylnaphthalen-7-yl)acetamido)-N-hydroxybenzamide EHT 9710

A) 3-(2,2-Difluoro-2-(1,2,3,4-tetrahydro-1,1,4,4-tetramethylnaphthalen-6-yl)acetamido)benzoic acid 20 (407 mg, 1.02 mmol) was dissolved in $SOCl_2$ (5.7 mL) and two drops of DMF were added at 0° C. This mixture was stirred at 0° C. for 1 h then evaporated under vacuum and the crude product was dissolved in $CH_2Cl_2$ (5 mL). B) Hydroxylamine hydrochloride (3.18 g, 45.7 mmol) was dissolved in THF (41.17 mL) and water (8.25 mL) and $Et_3N$ (8.25 mL) at 0° C., the mixture was stirred at 0° C. for 1 h. Solution A) was added at 0° C. via syringe in B) and the mixture was stirred at 0° C. for 10 min and abandoned at RT for 19 h. The mixture was evaporated and the residue obtained was extracted with $CH_2Cl_2$ (3×50 mL) and washed with water (50 mL). The organic layer was washed with brine (2×50 mL), dried over $MgSO_4$, filtered and evaporated. The crude product was purified by column chromatography eluent (cyclohexane: EtOAc=98:02). 3-(2,2-Difluoro-2-(1,2,3,4-tetrahydro-1,1,4,4-tetramethylnaphthalen-7-yl)acetamido)-N-hydroxybenzamide EHT 9710 was obtained (40 mg, 10% yield) as an orange solid.

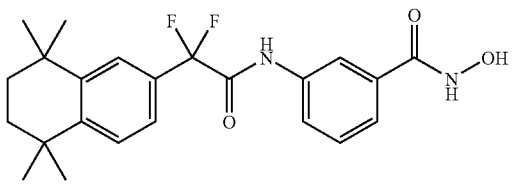

EHT 9710

MW: 416.46; Yield: 10%; Orange Solid; Mp (° C.): 119.2 (dec.).
$R_f$: 0.15 (cyclohexane :EtOAc=98:2).
$^1$H-NMR ($CD_3OD$, δ): 1.10 (s, 6H, 2×$CH_3$), 1.12 (s, 6H, 2×$CH_3$), 1.54 (s, 4H, 2×$CH_2$), 7.20-7.40 (m, 3H, ArH), 7.46 (d, 1H, J=5.9 Hz, ArH), 7.60 (d, 1H, J=6.5 Hz, ArH), 7.81 (d, 1H, J=4.3 Hz, ArH), 2×—NH— and OH exchanged.
MS-ESI m/z (rel. int.): 417.1 ([MH]$^+$, 100).
HPLC: Method A, detection UV 254 nm, EHT 9710 RT=6.45 min, peak area 98.2%.

Example 8

4-((2.2-difluoro-2-(1,2,3,4-tetrahydro-1,1,4,4-tetramethylnaphthalen-7-yl)acetamido)methyl)-N-hydroxybenzamide EHT 7800

Methyl 4-(aminomethyl)benzoate 4-aminomethyl benzoic acid (6.69 g, 44.09 mmol) was dissolved methanol (200 mL). $SOCl_2$ (12 mL) was added via syringe. The mixture was stirred at 70° C. for 3.5 h. After cooling, the reaction mixture was evaporated and the crude product was dissolved in CH$_2$Cl$_2$ (500 mL). The organic layer was washed with aqueous K$_2$CO$_3$ 10% (300 mL), dried with MgSO$_4$, filtered and evaporated. Methyl 4-(aminomethyl)benzoate was obtained (5.78 g, 79%) as a white solid.

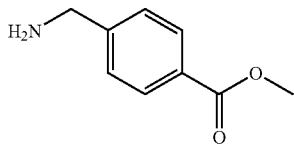

MW: 165.19; Yield: 79%; White Solid; Mp (° C.): 73.3.
$^1$H-NMR (CDCl$_3$, δ): 1.53 (s, 2H, NH$_2$), 3.94 (s, 1H, CH$_3$), 3.96 (s, 2H, N—CH$_2$), 7.39 (d, 2H, J=8.4 Hz, ArH), 8.02 (d, 2H, J=8.4 Hz, ArH).

Methyl 4-((2,2-difluoro-2-(1,2,3,4-tetrahydro-1,1,4,4-tetramethylnaphthalen-6-yl)acetamido)methyl) benzoate 21

A) Difluoro-(5,5,8,8-tetramethyl-5,6,7,8-tetrahydronaphthalen-2-yl)-acetic acid 16 (306 mg, 1.08 mmol) was dissolved in SOCl$_2$ and two drops of DMF were added at 0° C. The mixture was stirred at 0° C. for 30 min then evaporated and the product was dissolved in CH$_2$Cl$_2$ (7 mL). B) Methyl 4-(aminomethyl)benzoate SLA 07006 (179 mg, 1.08 mmol) and DMAP (14 mg, 0.11 mmol) were dissolved in CH$_2$Cl$_2$ (7 mL) and Et$_3$N (1.5 mL) at 0° C. A) was added at 0° C. via syringe in B) and the resulting mixture was stirred at 0° C. for 10 min and abandoned at RT for 1 h. Aqueous NH$_4$Cl 5% (100 mL) was added and the mixture extracted with EtOAc (3×50 mL). The organic layer was washed with NaHCO$_3$ 5% (3×100 mL) and brine (3×100 mL), dried over MgSO$_4$, filtered and evaporated in vacuo. The crude product was purified by flash chromatography using as eluent cyclohexane:EtOAc=9:1. Methyl 4-((2,2-difluoro-2-(1,2,3,4-tetrahydro-1,1,4,4-tetramethylnaphthalen-6-yl)acetamido)methyl)-benzoate 21 was obtained (0.27 g, 58% yield) as a beige solid.

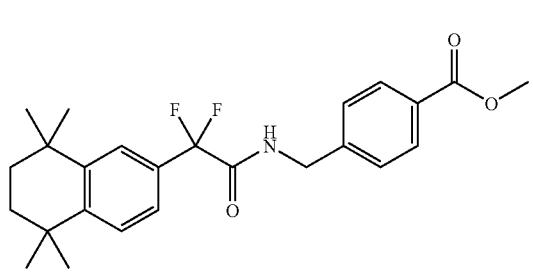

MW: 429.50; Yield: 58%; Beige Solid; Mp (° C.): 125.5.
R$_f$: 0.30 (cyclohexane:EtOAc=90:10).
$^1$H-NMR (CDCl$_3$, δ): 1.27 (s, 6H, 2×CH$_3$), 1.28 (s, 6H, 2×CH$_3$), 1.69 (s, 4H, 2×CH$_2$), 3.92 (s, 1H, CH$_3$), 4.57 (d, 2H, J=6.0 Hz, N—CH$_2$), 6.81 (s, 1H, NH), 7.29-7.41 (m, 4H, ArH), 7.52 (s, 1H, ArH), 8.00 (d, 2H, J=8.2 Hz, ArH).

4-((2,2-Difluoro-2-(1,2,3,4-tetrahydro-1,1,4,4-tetramethylnaphthalen-7-yl)acetamido)methyl)-N-hydroxybenzamide EHT 7800

A) Hydroxylamine hydrochloride (4.70 g, 67.6 mmol) was dissolved in methanol (25 mL) at 45° C. for 10 min in flask 100 mL. B] Potassium hydroxyde (5.64 g, 100.5 mmol) was dissolved in methanol (15 mL) at 45° C. for 10 min in flask 50 mL. Solution B) was added in A) at 45° C. The mixture was stirred at 45° C. for 10 min and cooled. The mixture was filtered and 10 mL of the filtrate was added at RT via syringe to a solution of 3-(2,2-Difluoro-2-(1,2,3,4-tetrahydro-1,1,4,4-tetramethylnaphthalen-6-yl)acetamido)benzoic acid 21 (263 mg, 0.61 mmol) in methanol (10 mL). The resulting mixture was stirred for 2 h at RT and a solution of HCl 1M was added to pH=5. The product was extracted with ethyl acetate (3×50ML) and the organic layer was dried over MgSO$_4$, filtered and evaporated in vacuo. The crude product was purified by column chromatography using as eluent CH$_2$Cl$_2$:MeOH=95:5. 4-((2,2-Difluoro-2-(1,2,3,4-tetrahydro-1,1,4,4-tetramethylnaphthalen-7-yl)acetamido)methyl)-N-hydroxybenzamide EHT 7800 was obtained (12.5 mg, 5% yield) as a yellow solid.

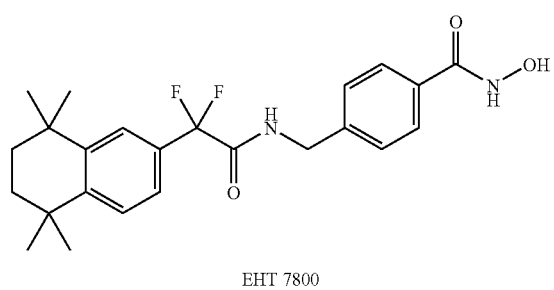

EHT 7800

MW: 430.49; Yield: 5%; Yellow Solid; Mp (° C.): 141.2 (dec.).
R$_f$: 0.35 (CH$_2$Cl$_2$:MeOH)=95:5.
$^1$H-NMR (CD$_3$OD, δ): 1.09 (s, 3H, 2×CH$_3$), 1.14 (s, 3H, 2×CH$_3$) 1.62 (s, 4H, 2×CH$_2$), 4.37 (s, 2H, —CH$_2$N), 7.18-7.28 (m, 3H, ArH), 7.33 (d, 1H, J=8.3 Hz, ArH), 7.41 (s, 1H, ArH ), 7.57 (d, 2H, J=8.0 Hz, ArH).

MS-ESI m/z (rel. int.): 431.1 ([MH]$^+$, 100).

HPLC: Method A, detection UV 254 nm, EHT 7800 RT=6.24 min, peak area 96.1%.

Example 9

N-(4-((hydroxycarbamoyl)difluoromethyl)phenyl)-5,6,7,8-tetrahydro-5,5,8,8-tetramethylnaphthalene-2-carboxamide EHT 4996

5,6,7,8-Tetrahydro-N-(4-iodophenyl)-5,5,8,8-tetramethylnaphthalene-2-carboxamide 22

A) 5,5,8,8-Tetramethyl-5,6,7,8-tetrahydro-naphthalene-2-carboxylic acid 2 (1.38 g, 5.94 mmol) was dissolved in SOCl$_2$ and two drops of DMF were added at 0° C. The mixture was stirred at 0° C. for 30 min and it was evaporated and this crude product was dissolved in CH$_2$Cl$_2$ (5 mL). B) 4-iodophenylamine (1.30 g, 5.94 mmol) and DMAP (73 mg, 0.59 mmol) were dissolved in CH$_2$Cl$_2$ (10 mL) and Et$_3$N (8.4 mL) was added at 0° C. The Mixture A) was added in B) at 0° C. via syringe and the resulting mixture was stirred at 0° C. for 10 min and abandoned at RT for 2.5 h. A solution of aqueous NH$_4$Cl 5% (50 mL) was added and the resulting mixture was extracted with EtOAc (3×150 mL). The organic layer was washed with NaHCO$_3$ (2×100 mL) and brine (3×100 mL) and dried with MgSO$_4$, filtered and evaporated. The crude product was purified by column chromatography using as eluent cyclohexane:EtOAc=90:10. 5,6,7,8-Tetrahydro-N-(4-iodophenyl)-5,5,8,8-tetramethylnaphthalene-2-carboxamide 22 was obtained (1.43 g, 56% yield) as a white solid.

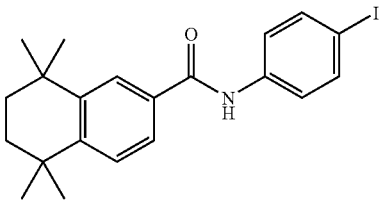

22

MW: 433.32; Yield: 56%; White Solid; Mp: 224.2° C.

R$_f$: 0.60 (cyclohexane:EtOAc=90:10).

$^1$H-NMR (CDCl$_3$, δ): 1.28 (s, 6H, 2×CH$_3$), 1.30 (s, 6H, 2×CH$_3$), 1.66 (s, 4H, 2×CH$_2$), 7.46 (d, 1H, J=8.3 Hz, ArH), 7.55-7.75 (m, 5H, ArH), 7.86 (d, 1H, J=1.6 Hz, ArH), 10.18 (s, 1H, NH).

$^{13}$C-NMR (CDCl$_3$, δ): 165.7, 148.3, 144.5, 139.1, 137.2 (2×C), 131.9, 126.5, 125.7, 124.8, 122.6 (2×C), 87.1, 34.4, 34.3, 34.1, 34.0, 31.5 (2×C), 31.3 (2×C).

MS-ESI m/z (rel. int.): 433.9 ([MH]$^+$, 100).

HPLC: Method A, detection UV 254 nm, RT=8.09 min, peak area 90%.

Ethyl 2-(4-(5,6,7,8-tetrahydro-5,5,8,8-tetramethylnaphthalene-2-carboxamido)phenyl)-2,2-difluoroacetate 23

Under a nitrogen atmosphere ethylbromodifluoroacetate (0.244 mL, 1.90 mmol) was added to a suspension of 5,6,7,8-tetrahydro-N-(4-iodophenyl)-5,5,8,8-tetramethylnaphthalene-2-carboxamide 22 (826 mg, 1.90 mmol), powder copper (99.999%, 588 mg) in anhydrous DMSO (16.7 mL). The reaction mixture was stirred at 58° C. for 18 h. After cooling, the mixture was poured in aqueous NH$_4$Cl 5% (150 mL). This mixture was extracted with EtOAc (5×150 mL). The organic layer was washed with aqueous NH$_4$Cl 5% (3×100 mL), brine (3×100 mL), dried over MgSO$_4$, filtered and evaporated. The crude product was purified by column chromatography using as eluent cyclohexane:EtOAc=95:5. Ethyl 2-(4-(5,6,7,8-tetrahydro-5,5,8,8-tetramethylnaphthalene-2-carboxamido)phenyl)-2,2-difluoroacetate 23 was obtained (0.61 g, 74.6% yield) as a white solid.

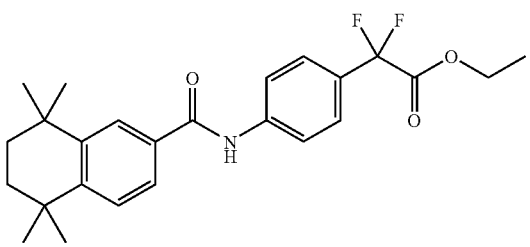

23

MW: 429.49; Yield: 74.6%; White Solid; Mp: 183.1° C.

R$_f$: 0.35 (cyclohexane:EtOAc=90:10).

$^1$H-NMR (CDCl$_3$, δ): 1.31 (t, 3H, J=7.1 Hz, CH$_3$), 1.31 (s, 6H, 2×CH$_3$), 1.33 (s, 6H, 2×CH$_3$), 1.72 (s, 4H, 2×CH$_2$), 4.30 (q, O—CH2, J=7.1 Hz), 7.41 (d, 1H, J=8.3 Hz, ArH), 7.55 (dd, 1H, J=2.0 Hz, J=8.3 Hz, ArH), 7.61 (d, 2H, J=8.7 Hz, ArH), 7.75 (d, 2H, J=8.7 Hz, ArH), 7.86 (s, 1H, J=2.0 Hz, ArH), 7.89 (s, 1H, NH).

MS-ESI m/z (rel. int.): 430.2 ([MH]$^+$, 100).

HPLC: Method A, detection UV 254 nm, RT=7.87 min, peak area 97%.

N-(4-((Hydroxycarbamoyl)difluoromethyl)phenyl)-5,6,7,8-tetrahydro-5,6,8,8-tetramethylnaphthalene-2-carboxamide EHT 4996

A) Hydroxylamine hydrochloride (2.34 g, 33.7 mmol) was dissolved in methanol (12 mL) at 45° C. for 10 min in a 50 mL round bottom flask. B) Potassium hydroxyde (2.81 g, 50.0 mmol) was dissolved in methanol (7 mL) at 45° C. for 10 min in 25 mL round bottom flask. The solution B) was added in A) at 45° C. This mixture was stirred at 45° C. for 10 min and cooled to RT. The mixture was filtered and 5 mL of the filtrate were added at RT via syringe to a solution of ethyl 2-(4-(5,6,7,8-tetrahydro-5,5,8,8-tetramethylnaphthalene-2-carboxamido)phenyl)-2,2-difluoroacetate 23 (0.10 g, 0.23 mmol) in methanol (4 mL). This mixture was stirred for 16 h at RT. A solution of HCl 1M was added to about pH=5. The aqueous layer was extracted with ethyl acetate (3×50 mL). The organic layer was dried over MgSO$_4$, filtered and evaporated in vacuo. N-(4-((Hydroxycarbamoyl)difluoromethyl)phenyl)-5,6,7,8-tetrahydro-5,5,8,8-tetramethylnaphthalene-2-carboxamide EHT 4996 was obtained (123 mg, 97% yield) as an orange solid.

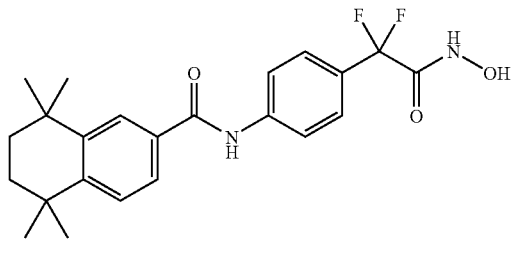

EHT 4996

MW: 416.46; Yield: 97%; Orange Solid; Mp (° C.): 179.3.

R$_f$: 0.35 (CH$_2$Cl$_2$:MeOH=95:5).

$^1$H-NMR (CD$_3$OD, δ): 1.40 (s, 6H, 2×CH$_3$), 1.43 (s, 6H, 2×CH$_3$), 1.83 (s, 4H, 2×CH$_2$), 7.55 (d, 1H, J=8.3 Hz, ArH), 7.68 (d, 2H, J=8.6 Hz, ArH), 7.77 ( dd, J=1.7 Hz, J=8.3 Hz, 1H, ArH), 7.93 (d, J=8.6 Hz, 2H, ArH), 8.02 (d, 1H, J=1.7 Hz, ArH), 2×NH and OH exchanged.

MS-ESI m/z (rel. int.): 417.2 ([MH]$^+$, 100).

HPLC: Method A, detection UV 254 nm, EHT 4996 RT=6.49 min, peak area 96.0%.

Example 10

N-(4-Hydroxycarbamoyl-Phenyl)-N'-(5,5,8,8-tetramethyl-5,6,7,8-tetrahydro-naphthalen-2-yl)-oxalamide EHT 0933

Methyl (1,2,3,4-tetrahydro-1,1,4,4-tetramethylnaphthalen-7-ylcarbamoyl)formate 24

To a solution of 5,6,7,8-tetrahydro-5,5,8,8-tetramethylnaphthalen-2-amine 6 in CH$_2$Cl$_2$ (20 mL) was added Et$_3$N (0.684 mL), and methoxyoxalylchloride (0.452 ml). The solution was stirred at 60° C. for 3 h and all the volatiles were evaporated to obtain a white solid that was purified using silica gel chromatography with EtOAc:Cyclohexane=15:85 to yield to methyl (1,2,3,4-tetrahydro-1,1,4,4-tetramethylnaphthalen-7-ylcarbamoyl)formate 24 (0.637 g, 90% yield).

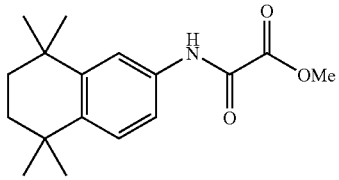

24

MW: 289.37; Yield: 90%; White Solid; Mp (° C.): 216.
$R_f$: 0.20 (EtOAc:Cyclohexane=15:85).
$^1$H-NMR (CDCl$_3$, δ): 1.27 (s, 6H, 2×CH$_3$), 1.28 (s, 6H, 2×CH$_3$), 1.68 (s, 4H, 2×CH$_2$), 3.96 (s, 3H, OCH$_3$), 7.31 (d, 1H, J=8.46 Hz, ArH), 7.46 (dd, 1H, J=8.46 Hz, J=2.36 Hz, ArH), 7.51 (d, 1H, J=2.26 Hz, ArH), 8.83 (s, 1H, NH).
MS-ESI m/z (rel. int.): 290.1 ([MH]$^+$, 100).
HPLC: Method A, detection UV 254 nm, RT=6.80 min, peak area 99.0%.

(1,2,3,4-tetrahydro-1,1,4,4-tetramethylnaphthalen-7-yl-carbamoyl)formic acid 25

A 25 mL round bottom flask equipped with a reflux condenser was charged with methyl (1,2,3,4-tetrahydro-1,1,4,4-tetramethylnaphthalen-7-ylcarbamoyl)formate 24 (0.200 g, 0.691 mmol), MeOH (10 mL) and KOH (0.078 g, 1.382 mmol). The reaction mixture was stirred for 3 h at reflux, evaporated to dryness and partitioned between EtOAc and H$_2$O. 6N HCl was added to reach acidic pH and the organic layer was separated, washed with water, brine, dried with Na$_2$SO$_4$, filtered and concentrated on a rotary evaporator to give (1,2,3,4-tetrahydro-1,1,4,4-tetramethylnaphthalen-7-yl-carbamoyl)formic acid as a white solid 25 (0.157 g, 83% yield).

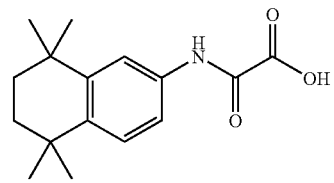

25

MW: 275.34; Yield: 83%; White Solid; Mp (° C.): 176.4.
$R_f$: 0.2 (MeOH:CH$_2$Cl$_2$=5:95).
$^1$H-NMR (CDCl$_3$, δ): 1.27 (s, 2×CH$_3$), 1.29 (s, 6H, 2×CH$_3$), 1.69 (s, 4H, 2×CH$_2$), 7.34 (d, 1H, J=8.53 Hz, ArH), 7.43 (dd, 1H, J=8.53 Hz, J=2.35 Hz, ArH), 7.49 (d, 1H, J=2.31 Hz, ArH), 8.92 (s, 1H, NH), CO$_2$H not seen.
MS-ESI m/z (rel. int.): 276.2 ([MH]$^+$, 40), 192.1 (100).
HPLC: Method A, detection UV 254 nm, RT=6.55 min, peak area 98.9%.

4-[(5,5,8,8-Tetramethyl-5,6,7,8-tetrahydro-naphthalen-2-ylaminooxalyl)-amino]-benzoic acid methyl ester 26

(1,2,3,4-Tetrahydro-1,1,4,4-tetramethylnaphthalen-7-yl-carbamoyl)formic acid 25 (0.10 g, 0.36 mmol) was dissolved in SOCl$_2$ (5 mL) at 0° C. A drop of DMF was added and the mixture was stirred for 0.5 h. The SOCl$_2$ was removed under vacuum and the crude acid chloride was dissolved in CH$_2$Cl$_2$ (5 mL). Methyl 4-aminobenzoate (0.06 g, 0.40 mmol) and triethylamine (0.04 mg, 0.40 mmol) were added and the mixture was stirred at 25° C. for 2 h. The mixture was poured into H$_2$O and the product was extracted with CH$_2$Cl$_2$. The organic layer was washed successively with HCl (2M), NaHCO$_{3(sat)}$, NaCl$_{(sat)}$, dried over MgSO$_4$, filtrated and evaporated to give a white crude solid that was purified using silica gel with 10% [v/v] EtOAc in cyclohexane. 4-[(5,5,8,8-Tetramethyl-5,6,7,8-tetrahydro-naphthalen-2-ylaminooxalyl)-amino]-benzoic acid methyl ester 26 (0.040 g, 27% yield) was obtained as a white solid.

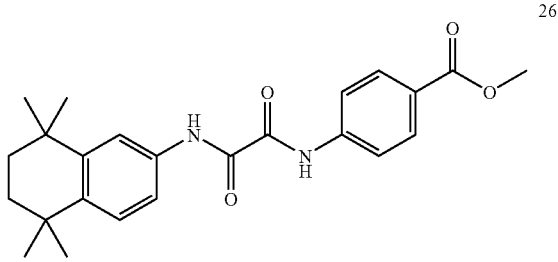

26

MW: 408.49; Yield: 27%; White Solid; Mp (° C.) 202.
$R_f$: 0.3 (MeOH:CH$_2$Cl$_2$=5:95).
$^1$H-NMR (CDCl$_3$, δ): 1.28 (s, 6H, 2×CH$_3$), 1.29 (s, 6H, 2×CH$_3$), 1.70 (s, 4H, 2×CH$_2$), 3.92 (s, 3H, OCH$_3$), 7.33 (d, 1H, J=8.5 Hz, ArH), 7.47 (dd, 1H, J=8.5 Hz, 2.3, ArH), 7.56 (d, 1H, J=2.3 Hz, ArH), 7.76 (d, 2H, J=8.7 Hz, ArH), 8.07 (d, 2H, J=8.7 Hz, ArH), 9.27 (s, 1H, NH), 9.61 (s, 1H, NH).
MS-ESI m/z (rel. int.): 409.1 ([MH]$^+$, 100).
HPLC: Method A, detection UV 254 nm, RT=7.80 min, peak area 96.7%.

N-(4-Hydroxycarbamoyl-phenyl)-N'-(5,5,8,8-tetramethyl-5,6,7,8-tetrahydro-naphthalen-2-yl)-oxalamide EHT 0933

To a solution of 4-[(5,5,8,8-tetramethyl-5,6,7,8-tetrahydro-naphthalen-2-ylaminooxalyl)-amino]-benzoic acid methyl ester 26 (0.040 g, 0.098 mmol) in MeOH (1 mL) was added an hydroxylamine solution (1.76 M, 2 mL) in MeOH and the reaction mixture was stirred 3 h at room temperature under magnetic stirring. The reaction mixture was adjusted to pH 5 with HCl 1M, concentrated and the residue was partitioned between EtOAc and H$_2$O. The organic layer was dried with Na$_2$SO$_4$ and the product was precipitated in CH$_3$CN to give N-(4-hydroxycarbamoyl-phenyl)-N'-(5,5,8,8-tetramethyl-5,6,7,8-tetrahydro-naphthalen-2-yl)-oxalamide EHT 0933 (0.012 g, 30% yield) as beige solid.

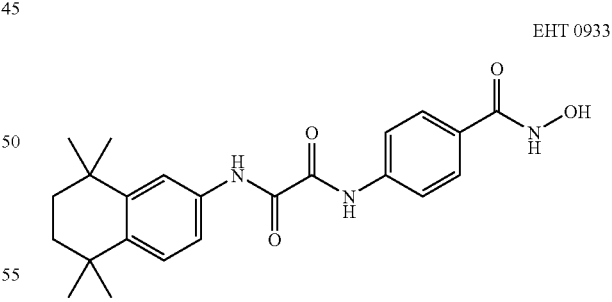

EHT 0933

MW: 409.48; Yield: 30%; White Solid; Mp (° C.): 244.3.
$R_f$: 0.30 (MeOH:CH$_2$Cl$_2$=5:95).
$^1$H-NMR (CD$_3$OD, δ): 1.16 (s, 6H, 2×CH$_3$), 1.18 ( s, 6H, 2×CH$_3$), 1.59 (s, 4H, 2×CH$_2$), 7.20 (d, 1H, J=8.58, ArH), 7.40 (d, 1H, J=8.49, ArH), 7.59 (s, 1H, ArH), 7.66 (d, 2H, J=8.64 Hz, ArH), 7.78 (d, 2H, J=8.51 Hz, ArH), 3×NH and OH exchanged.
MS-ESI m/z (rel. int.): 410.1 ([MH]$^+$, 100).
HPLC: Method A, detection UV 254 nm, EHT 0933 RT=6.50 min, peak area 95.9%.

Example 11

N-(4-hydroxycarbamoyl-benzyl)-N'-(5,5,8,8-tetramethyl-5,6,7,8-tetrahydro-naphthalen-2-yl)-oxalamide EHT 6028

4-{[(5,5,8,8-Tetramethyl-5,6,7,8-tetrahydro-naphthalen-2-ylaminooxalyl)-amino]-methyl}-benzoic acid methyl ester EBE 06018

(1,2,3,4-Tetrahydro-1,1,4,4-tetramethylnaphthalen-7-yl-carbamoyl)formic acid EBE 06006 (0.165 g, 0.60 mmol) was dissolved in SOCl$_2$ (5 mL) at 0° C. A drop of DMF was added and the mixture was stirred for 30 min. The SOCl$_2$ was removed under vacuum and the crude acid chloride was dissolved in CH$_2$Cl$_2$ (5 mL). Methyl 4-methylaminobenzoate (0.108 g, 0.66 mmol) and triethylamine (0.092 ml, 0.66 mmol) were added and the mixture was stirred at 25° C. for 2 h. The mixture was poured into H$_2$O and the product was extracted with CH$_2$Cl$_2$. The organic layer was washed successively with a solution of HCl 2M, saturated aqueous NaHCO$_3$, brine, dried over MgSO$_4$, filtered and evaporated to give a white crude solid. The crude product was purified using silica gel with 10% [v/v] EtOAc in cyclohexane. 4-{[(5,5,8,8-Tetramethyl-5,6,7,8-tetrahydro-naphthalen-2-ylaminooxalyl)-amino]-methyl}-benzoic acid methyl ester EBE 06018 (0.070 g, 46% yield) was obtained as a white solid.

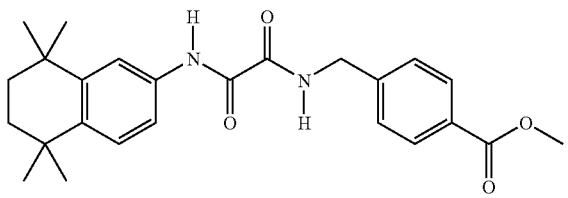

EBE06018

MW: 422.5; Yield: 46%; White Solid; Mp (° C.): 136.0.
R$_f$: 0.3 (EtOAc:cyclohexane=20:80).
$^1$H-NMR (CDCl$_3$, δ): 1.26 (s, 12H, 4×CH$_3$), 1.68 (s, 4H, 2×CH$_2$), 3.91 (s, 3H, OCH$_3$), 4.59 (d, 2H, J=6.3 Hz, CH$_2$), 7.27 (dd, 1H, J=1.1, J=8.5 Hz, ArH), 7.35 (d, 2H, J=8.35, ArH), 7.42 (dd, 1H, J=2.3, J=8.5 Hz, ArH), 7.51 (d, 1H, J=2.3 Hz, ArH), 8.00 (dd, 2H, J=1.7 Hz, J=6.69 Hz, ArH), 8.19 (t, 1H, J=6.1 Hz, NH), 9.27 (s, 1H, NH).
HPLC: Method A, detection at 254 nm, EBE 06018 RT=7.38 min, peak area 94.7%.

N-(4-Hydroxycarbamoyl-benzyl)-N'-(5,5,8,8-tetramethyl-5,6,7,8-tetrahydro-naphthalen-2-yl)-oxalamide EHT 6028.

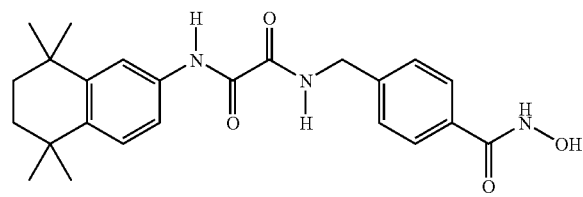

EHT 6028

To a solution of 4-{[(5,5,8,8-tetramethyl-5,6,7,8-tetrahydro-naphthalen-2-ylaminooxalyl)-amino]-methyl}-benzoic acid methyl ester EBE 06018 (70 mg, 0.17 mmol) in MeOH (2 mL) was added an hydroxylamine solution (1.76 M, 2 mL) in MeOH and the reaction mixture was stirred for 1 h at room temperature under magnetic stirring. The reaction mixture was adjusted to pH 5, concentrated and the residue was partitioned between EtOAc and H$_2$O. The organic layer was dried with Na$_2$SO$_4$, filtered and evaporated. The obtained crude product was recrystallized at 80° C. in CH$_3$CN to give N-(4-hydroxycarbamoyl-benzyl)-N'-(5,5,8,8-tetramethyl-5,6,7,8-tetrahydro-naphthalen-2-yl)-oxalamide EHT 6028 (0.020 g, 28% yield) as a beige solid after filtration and drying to the vacuum pump.

MW: 423.5; Yield: 28%; Beige Solid; Mp (° C.): 145.2.
R$_f$: 0.2 (MeOH:CH$_2$Cl$_2$=5:95).
$^1$H-NMR (CD$_3$OD, δ): 1.26 (s, 6H, 2×CH$_3$), 1.28 (s, 6H, 2×CH$_3$), 1.70 (s, 4H, 2×CH$_2$), 4.54 (s, 2H, CH$_2$), 7.30 (d, 1H, J=1.1, J=8.5 Hz, ArH), 7.40-7.50 (m, 3H, ArH), 7.65-7.76 (m, 3H, ArH), 3×NH & OH exchanged.
HPLC: Method A, detection at 254 nm, EHT 6028 RT=6.18 min, peak area 95.0%.
MS-ESI m/z (rel. int.): 424.1 ([MH]$^+$, 20).

Example 12

Pharmacology

This example discloses the screening assay used to illustrate the biological activity of the different compounds.

The discovery of novel HDAC inhibitors, through in vitro screening, involves the use of a convenient and sensitive assay for the measurement of inhibition of HDAC activity.

The classical assay uses radiolabeled histone from animal or cell culture, or peptides derived from histone peptide sequences as substrates. Deacetylation is then monitored by extraction of the liberated [$^3$H]-acetic acid via scintillation counting. However, due to the involvement of radioactivity and the problem of standardization of radiolabeled histones preparation, this assay is incompatible for high throughput screening for drug discovery.

Therefore, a fast, non isotopic method has been chosen that relies on a fluorescent HDAC substrate. This assay is a two step enzymatic reaction. The substrate used is a peptidic substrate with a ε-acetylated lysyl moiety followed by a 4-methylcoumarin-7-amide (AMC) moiety at their carboxy terminus. In the first reaction catalysed by HDACs, acetate is released from ε-acetylated lysine residue. In the second reaction, the deacetylated peptides are recognized as substrate by trypsin, which cleaves the deacetylated peptide after the lysine residue. This cleavage releases the AMC and the fluorescence is monitored by a fluorometer.

Methods

In order to evaluate the effect of one compound on HDAC activity, the HDAC Fluorescent Activity Assay/Drug Discovery Kit® developed by Biomol and based on the two step enzymatic reaction described above was used with modifications. The substrate of the Biomol assay, called Fluor de Lys™, comprises an acetylated lysine side chain with an AMC moiety.

Two well-known HDAC inhibitors have been used as positive controls: Trichostatin A (TSA), a natural product isolated from *Streptomyces hygroscopicus*, and suberoylanilide hydroxamic acid (SAHA), a synthetic compound. It has been demonstrated that HDAC activity is inhibited by both TSA (1.4-2.6 nM) and SAHA (127-259 nM) depending of the HDAC activity assay used. TSA and SAHA have been reported to inhibit cell growth, induce terminal differentiation, and prevent the formation of tumours in mice.

Briefly, assay buffer (25 mM tris/HCl pH=8, 137 mM NaCl, 2.7 mM KCl, 1 mM MgCl$_2$), diluted positive controls or diluted test inhibitors (11 concentrations ranging from 0 nM to 50 μM) are mixed into a 96 microtiter plate. Then, 5 μg of Hela (human cervical cancer cell line) cells nuclear extract is added in each well. The enzymatic reaction is initiated by the addition of the diluted Fluor de Lys™ substrate and the microplate is incubated at room temperature (e.g. 25° C.) for 0.5 h. In order to stop the reaction and to produce the fluorophore release, 50 μl of the Fluor de Lys™ Developer solution is added in each well and the microplate is incubated at room temperature (e.g. 25° C.) for 0.25 h. Finally, the fluorescence is measured by a fluorimeter (Fluoroskan Ascent FL, Thermolabsystem) at excitation wavelength of 360 nm and emission wavelength of 460 nm. Data was analysed using the GraphPad Prism® software and $IC_{50}$ (dose of compound leading to 50% of HDAC activity) was calculated from the dose-response curve.

Results

In order to determine the capacity of the compounds of this invention to affect HDAC activity, $IC_{50}$ were calculated using the HDAC activity assay as described in the method.

In parallel, the two reference compounds, TSA and SAHA, were tested in order to validate that the method is well suited to screening applications to identify novel HDAC inhibitors. As presented in FIG. 10, semi logarithmic plots analysed by GraphPad Prism® software indicate $IC_{50}$ of 1.4+/−0.5 nM for TSA (FIG. 10a) and 20 nM for SAHA (FIG. 10b) which are in the range of the $IC_{50}$ values reported recently for the same enzyme/inhibitor combination and a similar fluorescent substrate.

In our model, 4 compounds have been shown to have activity under 5 μM. The compound showing the highest effect on HDAC activity is EHT 9299 ($IC_{50}$=424+/−22 nM), followed by EHT 7706 ($IC_{50}$=1.18+/−0.37 μM), EHT 7800 ($IC_{50}$=4.1 μM) and finally EHT 3741 ($IC_{50}$=5.13+/−0.67 μM).

These results illustrate the ability and the efficiency of the compounds of this invention (especially EHT 9299) to affect specifically HDAC enzymatic activity.

The invention claimed is:

1. A compound, which is selected from the group consisting of:
   N-(4-(Hydroxycarbamoyl)phenyl)-5,6,7,8-tetrahydro-5,5,8,8-tetramethylnaphthalene-2-carboxamide,
   N-(4-(2-Aminophenylcarbamoyl)phenyl)-5,6,7,8-tetrahydro-5,5,8,8-tetramethyl-naphthalene-2-carboxamide,
   N-(1,2,3,4-Tetrahydro-1,1,4,4-tetramethylnaphthalen-6-yl)-N'-hydroxyterephthalamide,
   4-((E)-2-(1,2,3,4-tetrahydro-1,1,4,4-tetramethylnaphthalen-6-yl)vinyl)-N-hydroxybenzamide,
   4-((Z)-2-(1,2,3,4-tetrahydro-1,1,4,4-tetramethylnaphthalen-6-yl)vinyl)-N-hydroxybenzamide,
   4-(2,2-difluoro-2-(1,2,3,4-tetrahydro-1,1,4,4-tetramethylnaphthalen-7-yl)acetamido)-N-hydroxybenzamide,
   3-(2,2-difluoro-2-(1,2,3,4-tetrahydro-1,1,4,4-tetramethylnaphthalen-7-yl)acetamido)-N-hydroxybenzamide,
   4-((2,2-difluoro-2-( 1,2,3,4-tetrahydro-1,1,4,4-tetramethylnaphthalen-7-yl)acetamido)methyl)-N-hydroxybenzamide,
   N-(4-((hydroxycarbamoyl)difluoromethyl)phenyl)-5,6,7,8-tetrahydro-5,5,8,8-tetramethylnaphthalene-2-carboxamide,
   N-(4-Hydroxycarbamoyl-phenyl)-N'-(5,5,8,8-tetramethyl-5,6,7,8-tetrahydro-naphthalen-2-yl)-oxalamide and
   N-(4-Hydroxycarbamoyl-benzyl)-N'-(5,5,8,8-tetramethyl-5,6,7,8-tetrahydro-naphthalen-2-yl)-oxalamide.

2. A compound, which is selected from the group consisting of:
   4-(2,2-Difluoro-2-(1,2,3,4-tetrahydro-1,1,4,4-tetramethylnaphthalen-7-yl)acetamido)-N-hydroxybenzamide,
   N-(1,2,3,4-Tetrahydro-1,1,4,4-tetramethylnaphthalen-6-yl)-N'-hydroxyterephthalamide,
   4-((2,2-Difluoro-2-(1,2,3,4-tetrahydro-1,1,4,4-tetramethylnaphthalen-7-yl)acetamido)methyl)-N-hydroxybenzamide and
   N-(4-(Hydroxycarbamoyl)phenyl)-5,6,7,8-tetrahydro-5,5,8,8-tetramethylnaphthalene-2-carboxamide.

3. A pharmaceutical composition comprising at least one compound, as defined in claim 1, and a pharmaceutically acceptable vehicle or support.

4. A method for the treatment of cancers, comprising the administration to a subject in need thereof of an effective amount of a compound as defined in claim 1.

5. A method according to claim 4, wherein the cancer is selected from promyelocytic leukaemia, prostate cancer, ovarian cancer, pancreas cancer, lung cancer, breast cancer, liver cancer, head and neck cancer, colon cancer, bladder cancer, non-Hodgkin's lymphoma cancer and melanoma.

6. A method for reducing cancer cell proliferation, comprising the administration to a subject in need thereof of an effective amount of a compound as defined in claim 1.

7. The method of claim 4 wherein cancer is promyelocytic leukaemia.

* * * * *